(12) United States Patent
Myers et al.

(10) Patent No.: US 12,090,706 B2
(45) Date of Patent: Sep. 17, 2024

(54) BIOPRINTER FOR FABRICATING 3D CELL CONSTRUCTS

(71) Applicant: Inventia Life Science Pty Ltd, Alexandria (AU)

(72) Inventors: Samuel James Myers, Kingsford (AU); Andrew Leon Vella, Bexley (AU); Theophile Allard, Talloires (FR); Kieran Joseph O'Mahoney, Bantry County Cork (IE); Aidan Patrick O'Mahony, Mascot (AU); Julio Cesar Caldeira Ribeiro, Waterloo (AU)

(73) Assignee: Inventia Life Science Pty Ltd, Alexandria (AU)

( * ) Notice: Subject to any disclaimer, the term of this patent is extended or adjusted under 35 U.S.C. 154(b) by 0 days.

(21) Appl. No.: 16/770,254

(22) PCT Filed: Dec. 7, 2018

(86) PCT No.: PCT/AU2018/000249
§ 371 (c)(1),
(2) Date: Jun. 5, 2020

(87) PCT Pub. No.: WO2019/109127
PCT Pub. Date: Jun. 13, 2019

(65) Prior Publication Data
US 2020/0384690 A1    Dec. 10, 2020

(30) Foreign Application Priority Data

Dec. 8, 2017    (AU) ................................ 2017904946

(51) Int. Cl.
*B29C 64/321*    (2017.01)
*B29C 64/112*    (2017.01)
(Continued)

(52) U.S. Cl.
CPC .......... *B29C 64/321* (2017.08); *B29C 64/112* (2017.08); *B29C 64/245* (2017.08);
(Continued)

(58) Field of Classification Search
CPC ... B29C 64/321; B29C 64/364; B29C 64/112; B29C 64/245; B29C 64/255;
(Continued)

(56) References Cited

U.S. PATENT DOCUMENTS 6,470,226 B1 * 10/2002 Olesen ............. G01N 33/48728
700/56
6,994,429 B1    2/2006 McEntee et al.
(Continued)

FOREIGN PATENT DOCUMENTS

CN    103333853 A    10/2013
CN    105722662 A    6/2016
(Continued)

OTHER PUBLICATIONS

English translation of JP200947613 (Year: 2009).*
(Continued)

*Primary Examiner* — Galen H Hauth
*Assistant Examiner* — Baileigh Kate Darnell
(74) *Attorney, Agent, or Firm* — Morgan, Lewis & Bockius LLP

(57) ABSTRACT

A bioprinter for fabricating three-dimensional (3D) cell constructs, the bioprinter comprising one or more holding reservoirs for holding a fluid sample; a printstage for holding a sample container and supporting a substrate on which a 3D cell construct is to be printed; a sample loading system in fluid communication with the one or more holding reservoirs, the sample loading system configured to load a sample from a sample container into the one or more holding reservoirs; a pump in fluid communication with the sample
(Continued)

loading system, the pump configured to draw the sample out of a sample container and pump the sample into the one or more holding reservoirs; and a droplet dispensing system in fluid communication with the one or more reservoirs, the droplet dispensing system configured to print sample droplets from the one or more reservoirs onto a substrate supported by the printstage.

18 Claims, 12 Drawing Sheets

(51) Int. Cl.
| | |
|---|---|
| B29C 64/245 | (2017.01) |
| B29C 64/255 | (2017.01) |
| B29C 64/364 | (2017.01) |
| B33Y 10/00 | (2015.01) |
| B33Y 30/00 | (2015.01) |
| B33Y 40/00 | (2020.01) |
| B33Y 80/00 | (2015.01) |
| C12M 3/00 | (2006.01) |
| C12N 5/00 | (2006.01) |
| B29L 31/40 | (2006.01) |

(52) U.S. Cl.
CPC .......... *B29C 64/255* (2017.08); *B29C 64/364* (2017.08); *B33Y 10/00* (2014.12); *B33Y 30/00* (2014.12); *B33Y 40/00* (2014.12); *B33Y 80/00* (2014.12); *C12M 21/08* (2013.01); *C12N 5/0062* (2013.01); *B29L 2031/40* (2013.01); *C12N 2513/00* (2013.01)

(58) Field of Classification Search
CPC ....... B29C 64/25; B29C 64/209; B33Y 10/00; B33Y 30/00; B33Y 40/00; B33Y 70/00; B33Y 80/00; C12N 5/0062; C12N 2513/00; C12M 21/08; B29L 2031/40
See application file for complete search history.

(56) References Cited

U.S. PATENT DOCUMENTS

| | | | |
|---|---|---|---|
| 2004/0237822 A1 | 12/2004 | Boland et al. | |
| 2009/0263849 A1* | 10/2009 | Sun | B01L 3/502707 435/29 |
| 2013/0089642 A1* | 4/2013 | Lipson | B29C 64/106 426/115 |
| 2015/0035206 A1* | 2/2015 | Maggiore | B29C 64/25 264/401 |
| 2015/0037445 A1* | 2/2015 | Murphy | B29C 64/182 425/131.1 |
| 2015/0110911 A1* | 4/2015 | Snyder | B29C 64/321 95/12 |
| 2015/0375453 A1* | 12/2015 | Yost | C12N 11/04 435/174 |
| 2016/0083681 A1* | 3/2016 | Tavana | B29C 64/112 264/308 |
| 2016/0288414 A1* | 10/2016 | Ozbolat | A61F 2/30942 |
| 2017/0029765 A1 | 2/2017 | Vellinger et al. | |
| 2017/0121674 A1* | 5/2017 | Yoneda | C12M 33/04 |
| 2017/0128601 A1* | 5/2017 | DeCiccio | A61L 2/22 |
| 2017/0184839 A1 | 6/2017 | Tigelaar et al. | |
| 2018/0243980 A1* | 8/2018 | Erb | B29C 64/295 |
| 2018/0326665 A1* | 11/2018 | Gatenholm | B29C 64/393 |
| 2018/0339455 A1* | 11/2018 | Cohen | B33Y 40/00 |
| 2019/0168456 A1* | 6/2019 | Greyf | B29C 64/20 |
| 2020/0316252 A1* | 10/2020 | Cohen | A61L 27/3821 |

FOREIGN PATENT DOCUMENTS

| | | |
|---|---|---|
| EP | 1 101 616 A1 | 5/2001 |
| JP | 2002-507278 A | 3/2002 |
| JP | 2003-114238 A | 4/2003 |
| JP | 2009-47613 A | 3/2009 |
| WO | WO 2014/197999 A1 | 12/2014 |
| WO | WO 2015/017579 A1 | 2/2015 |
| WO | 2017/040675 A1 | 3/2017 |
| WO | WO 2017/184839 A1 | 10/2017 |

OTHER PUBLICATIONS

Faulkner-Jones A., "Development of a valve-based cell printer for the formation of human embryonic stem cell spheroid aggregates", Biofabrication 5, 2013, dio:10.1088/1758-5082/5/1/015013.
International Search Report issued in corresponding International Patent Application No. PCT/AU2018/000249.

* cited by examiner

BIOPRINTER FOR FABRICATING 3D CELL CONSTRUCTS

TECHNICAL FIELD

The technology relates to a bioprinter for fabricating three-dimensional (3D) cell constructs, processes for bioprinting 3D cell constructs, and bioprinted 3D cell constructs.

RELATED APPLICATION

This application is based on and claims priority to Australian provisional patent application No 2017904946 filed on 8 Dec. 2017, the content of which is incorporated by reference in its entirety.

BACKGROUND

The workhorse of in vitro cell biology is cell culture where primary or immortalized cells are simply plated onto plastic or glass surfaces. A number of cellular properties, such as in cell proliferation, differentiation and responses towards external stimuli, are fundamentally different for cells in two dimensional (2D) and the 3D environments found in vivo. Particularly for drug development and precision medicine programs, cell culture conditions that better reflect the 3D animal environments, and hence would limit the number of failed animal experiments, would be highly advantageous.

For example, in cancer cell biology, 3D models exhibit more in vivo tumor-like features including hypoxic regions, gradient distribution of chemical and biological factors and expression of pro-angiogenic and multidrug resistance proteins, compared to 2D cell culture models.

It is for this reason that 3D multicellular models, are generally regarded as superior models of in vivo systems than the more popular 2D cell culture.

Further, most cellular structures in multicellular biology are organised three-dimensionally. Numerous studies have reported the printing of cells using 3D bioprinting technology (reviewed in (Murphy and Atala, 2014)).

There exist many commercially available 3D bioprinters, for example: 3D-Bioplotter® by EnvisionTEC; BioScaffolder by GeSiM; Bio X by Cellink; BioFactory® by RegenHU; BioBot 2 by BioBots. The commercially available 3D bioprinters are most commonly based on microextrusion, thermal inkjet or piezoelectric inkjet technology. The commercially available 3D bioprinters most commonly utilise cartridges (e.g. Nordson Optimum® Syringe Barrels) for loading substances into the printer. Each one of these cartridges is often coupled to a single printhead. Maintenance of sterility is challenging during cartridge filling, handling, installation and removal.

The design of 3D models of organ or tissue architecture for 3D bioprinting applications have largely been based on:

1) noninvasive medical imaging technologies (e.g. computed tomography (CT) and magnetic resonance imaging (MRI)) for data collection; and 2) computer-aided design and computer-aided manufacturing (CAD-CAM) tools and mathematical modelling for information digitisation, generation of 3D-rendered models and generation of 2D cross-sectional images (Murphy and Atala, 2014; Horn and Harrysson, 2012).

There is a need for tools and techniques that facilitate application of 3D cell culture models in a scalable, repeatable and cost-effective manner to drug discovery, personalized medicine and general cell biology.

The present inventors have developed devices, systems and methods for fabricating in vitro 3D cell culture assays and arrays thereof.

SUMMARY

In a first aspect, the present invention provides a bioprinter for fabricating three-dimensional (3D) cell constructs, the bioprinter comprising:

one or more holding reservoirs for holding a fluid sample;

a printstage for holding a sample container and supporting a substrate on which a 3D cell construct is to be printed;

a sample loading system in fluid communication with the one or more holding reservoirs, the sample loading system configured to load a sample from a sample container into the one or more holding reservoirs;

a pump in fluid communication with the sample loading system, the pump configured to draw the sample out of a sample container and pump the sample into the one or more holding reservoirs; and a droplet dispensing system in fluid communication with the one or more reservoirs, the droplet dispensing system configured to print sample droplets from the one or more reservoirs onto a substrate supported by the printstage.

In an embodiment, the bioprinter further comprises a housing encompassing the one or more holding reservoirs, the printstage, the holder, the sample loading system, the pump, and the droplet dispensing system.

In an embodiment, the bioprinter further comprises an air flow system disposed in the housing, the air flow system configured to induce a laminar air flow within the housing.

In an embodiment, the air flow system comprises a fan to induce the laminar air flow in the housing In an embodiment, the air flow system comprises at least one air filter.

In an embodiment, the sample loading system comprises a needle for insertion into a sample container, the pump configured to draw fluid through the needle when the needle is inserted into the sample container.

In an embodiment, the bioprinter further comprises a first positioning unit coupled to the needle, the first positioning unit configured to insert the needle into a sample container and withdraw the needle from the sample container.

In an embodiment, the bioprinter further comprises a second positioning unit having a track, the second positioning unit coupled to the needle and the droplet dispensing system and configured to move the needle and the droplet dispensing system along the track of the second positioning unit.

In an embodiment, the bioprinter further comprises a third positioning unit having a track, the third positioning unit coupled to the print stage and configured to move the print stage along track of the third positioning unit.

In an embodiment, the track of the second positioning unit extends substantially perpendicularly to the track of the third positioning unit.

In an embodiment, the bioprinter further comprises a plurality of holding reservoirs, and the sample loading system configured to load a sample from the sample container into any one of the plurality of reservoirs.

In an embodiment, the sample container is a tray having a plurality of sample wells, the sample wells configured to contain samples, and the sample loading system is configured to load a sample from any one of the sample wells into any one of the holding reservoirs.

In an embodiment, the bioprinter further comprises a waste container configured to receive waste material from the sample loading system.

In an embodiment, the waste container is provided on the tray

In an embodiment, the pump is configured to draw the sample out of one of the holding reservoir and pump the sample out of the sample loading system.

In an embodiment, the bioprinter further comprises a pressure regulator coupled in fluid communication to each holding reservoir to regulate the pressure in each holding reservoir.

In an embodiment, the bioprinter further comprises a selector valve in fluid communication with the pump, the sample loading system, each holding reservoir, and the pressure regulator, the selector valve configured to selectively couple the pump in fluid communication to the sample loading system and each holding reservoir.

In an embodiment, the pressure regulator is removably coupled in fluid communication to a compressed air supply In a second aspect, the present invention provides a method of fabricating a three-dimensional cell construct comprising depositing droplets of one or more samples using the bioprinter of the first aspect.

In a third aspect, the present invention provides a method of fabricating a three-dimensional cell construct, the method comprising:

providing a bioprinter of the first aspect;

providing a substrate to the printstage;

providing a sample container to printstage, the sample container comprising a sample;

loading a sample into one of the holding reservoirs by the sample loading system; and printing the sample onto the substrate from the holding reservoir using the droplet dispensing system to form the three-dimensional cell construct.

There is also disclosed a bioprinter for fabricating 3D cell constructs, the bioprinter comprising:

a sample loading system for loading a sample from a sample container into a holding reservoir;

a selector valve in fluid communication with the holding reservoir for directing the sample into the holding reservoir;

a droplet dispensing system in fluid communication with the holding reservoir, the droplet dispensing system adapted to print sample droplets from the holding reservoir onto a substrate;

a control system to control operation of the sample loading system, the selector valve and the droplet dispensing system;

a laminar air flow system; and a housing encompassing the sample loading system, the selector valve, the droplet dispensing system and the laminar air flow system.

In an embodiment, the sample loading system comprises a plurality of sample containers and a plurality of holding reservoirs for holding a sample from each container.

In an embodiment the plurality of sample containers are housed in a removable sample tray.

In one embodiment, the removable sample tray comprises 10 positions for holding the sample containers in an array.

In an embodiment, the sample containers are vials having a cap and septum.

In an embodiment, the removable sample tray further includes a waste container for receiving waste from flushing the sample loading system.

In an embodiment, the removable sample tray further includes a cleaning container for cleaning the sample loading system, the selector valve, and droplet dispensing system.

In an embodiment, the sample loading system comprises a needle for insertion into the sample container, a pump operably coupled to the needle for transferring the sample in the sample container to the holding reservoir.

In an embodiment, the pump is a positive displacement pump.

In an embodiment, the pump is a peristaltic, diaphragm or syringe pump.

In an embodiment, the pump is operably reversible for resuspension of a sample in a container.

In an embodiment, the sample loading system further comprises a first positioning unit operably coupled to the needle, the first positioning unit for positioning the needle into puncturing-engagement with the sample container and out of puncturing-engagement with the sample container.

In an embodiment, the sample in the sample container can be cell suspension, water, ethanol, bio-ink, activator, cleaning solution, flushing fluid, cell culture media, or drug dispersed in solution.

In an embodiment, the sample in the sample container is sterile.

In an embodiment, the sample loading system further comprises a second positioning unit operably coupled to the needle, the second positioning unit for positioning the needle in two-dimensional space.

In an embodiment, the holding reservoir is an elongate tubing.

In an embodiment, the elongate tubing is coiled and encased in a chamber.

In an embodiment, the holding reservoir is formed of a spool of flexible tubing.

In an embodiment, the flexible tubing is made from Polytetrafluoroethylene (PTFE) tubing.

In an embodiment, the droplet dispensing system comprises at least one printhead operably coupled to the plurality of holding reservoirs and adapted to dispense sample droplets onto the substrate from each holding reservoir.

In an embodiment, the at least one printhead is an array of valves.

In an embodiment, each valve is a micro-solenoid valve.

In an embodiment, the samples are stored in the holding reservoirs upstream of the micro-solenoid valves.

In an embodiment, each holding reservoir has a respective printhead.

In an embodiment, each holding reservoir is coupled to a pressure regulator.

In an embodiment, a compressed air supply is coupled to the regulator manifold.

In an embodiment, each micro-solenoid valve is coupled to each pressure regulator.

In an embodiment, the droplet dispensing system includes a plurality of pressure regulators in a regulator manifold, at least one check valve, wherein the compressed air supply is operably coupled to each pressure regulator in the regulator manifold.

In an embodiment, the pressure regulator is coupled to the selector valve.

In an embodiment, the sample is taken from the sample container into the holding reservoir using the sample loading system, and taken from the holding reservoir into the printhead via operation of the droplet dispensing system, with the pressure regulator of the droplet dispensing system and the selector valve of the sample loading system operatively working to move the sample from the holding reservoir to the printhead.

In an embodiment, the droplet dispensing system further comprises a printstage for supporting the substrate.

In an embodiment, the substrate is a multi-well plate.

In an embodiment, the droplet dispensing system further comprises a third positioning unit operably coupled to the printstage, the third positioning unit for positioning the printstage in two-dimensional space.

In an embodiment, the control system records the identity of a sample in a sample container from a user input.

In an embodiment, the control system comprises a non-transitory computer readable medium including programmed instructions for operating the bioprinter.

In an embodiment, the non-transitory computer readable medium is located separately from the bioprinter and is operatively connectable to the bioprinter.

In an embodiment, the laminar flow system comprises a fan for drawing air into the housing, an air inlet for the air to flow into, filters and an air outlet.

In an embodiment, the fan is a centrifugal fan.

In an embodiment, the fan draws air into the front of the housing from underneath the printstage, around the sample loading system and through one or more filters and out of the housing.

In an embodiment, the fan draws air through a front access door of the bioprinter housing.

In an embodiment, the laminar flow system comprises two filters, one for exhaust air, one for receiving air towards the printstage.

In an embodiment, each filter is high efficiency particulate air (HEPA) filter.

In an embodiment, each filter receives about 50% of the airflow.

In an embodiment, the housing contains a hinged door to allow access to the interior of the bioprinter by a user.

In an embodiment, the removable sample tray is loadable into the bioprinter via the door.

In an embodiment, the removable sample tray has a lid.

In an embodiment, the housing has a recess to receive the sample tray lid and a lid for the multi-well plate.

In an embodiment, the sample container is loadable into the removable sample tray inside the bioprinter.

In a second aspect, there is provided a method of fabricating at least one three-dimensional cell construct by depositing a plurality of droplets of samples using a bioprinter according to the first aspect.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

In order that the present invention may be more clearly understood, preferred embodiments will be described with reference to the following drawings and examples.

DESCRIPTION OF EMBODIMENTS

Figure 1:
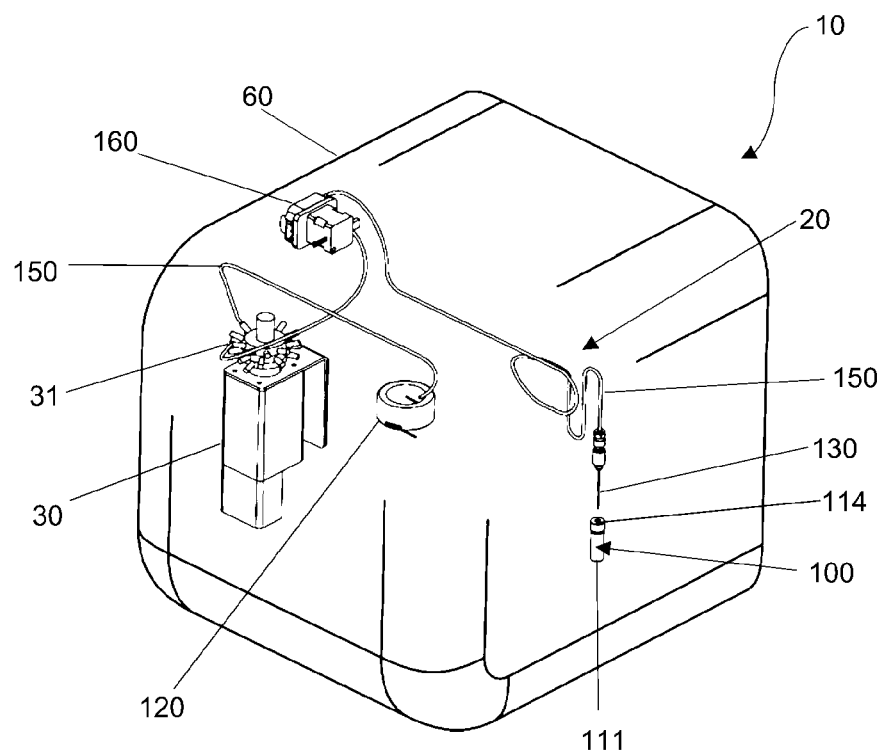
FIG. 1 is rear perspective view of a bioprinter for fabricating 3D cell constructs, illustrating a sample loading system.
Figure 2:
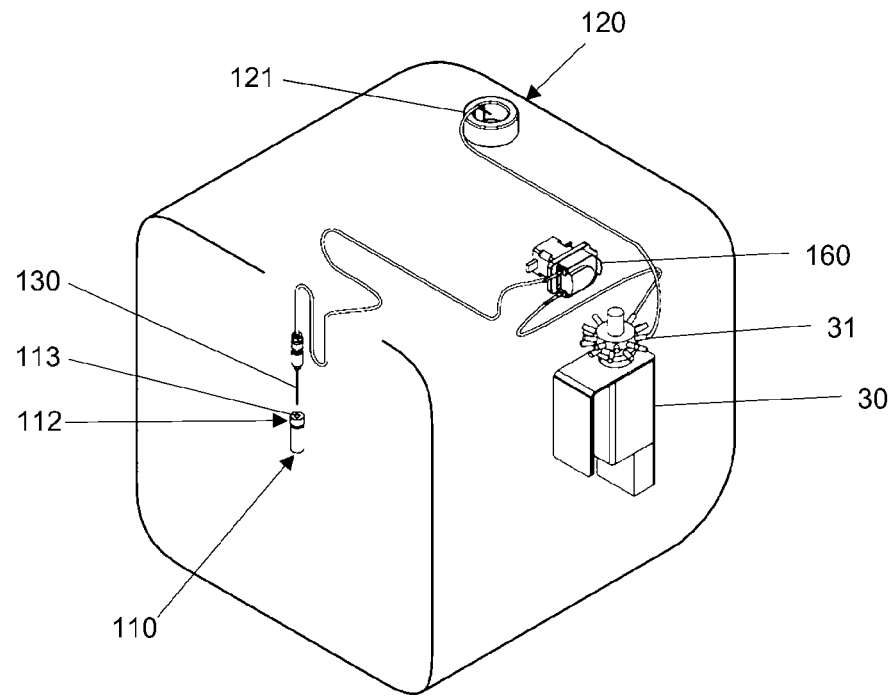
FIG. 2 is a front perspective view of the sample loading system of FIG. 1.
Figure 3:
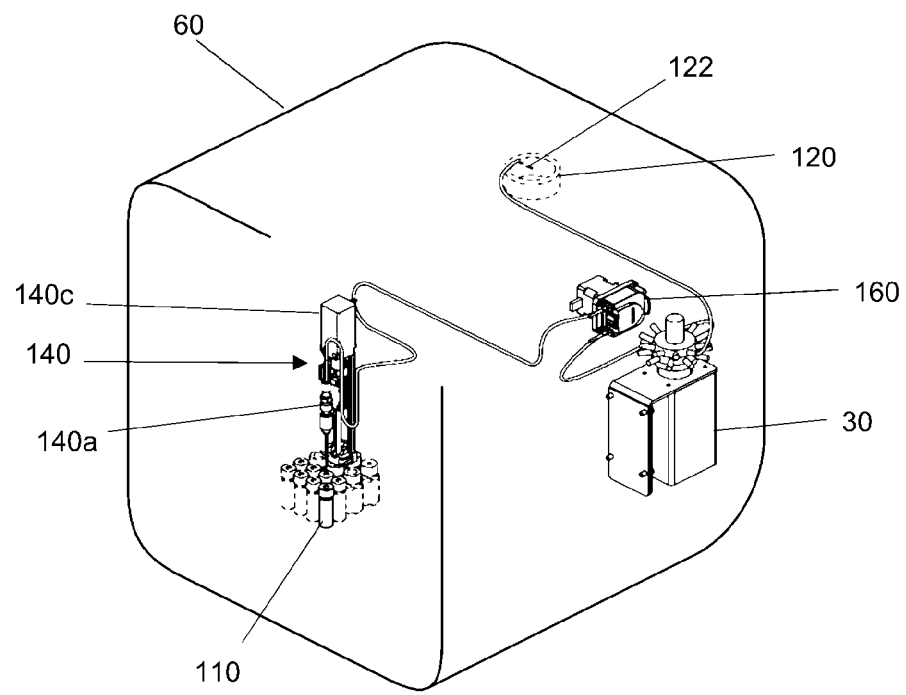
FIG. 3 is a front perspective view of the sample loading system, illustrating a plurality of sample containers each containing a sample.
Figure 4:
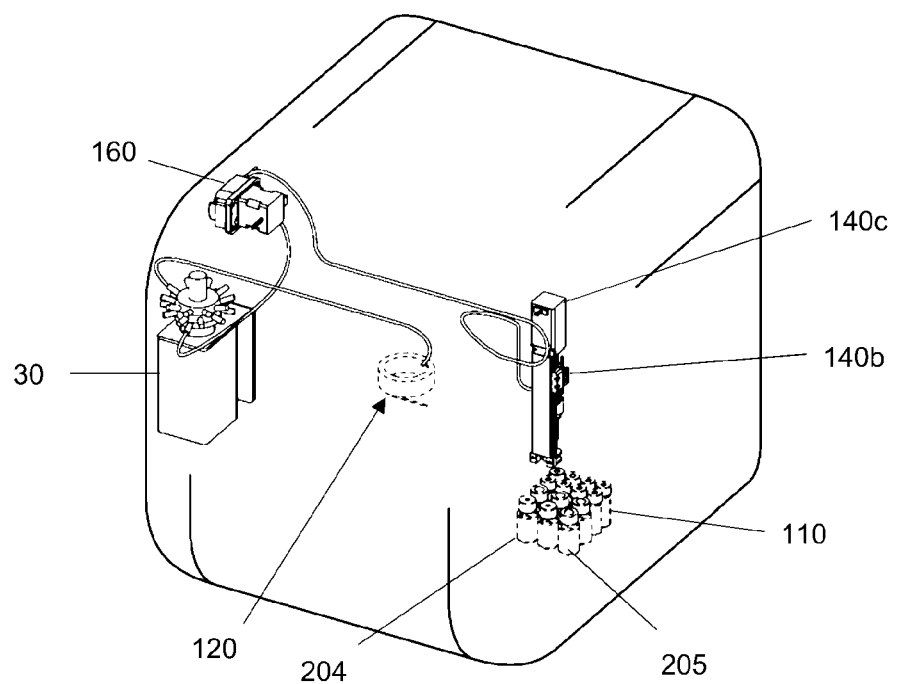
FIG. 4 is rear perspective view of the sample loading system of FIG. 3.

As illustrated in the drawings, there is disclosed herein a bioprinter 10 for fabricating 3D cell constructs. The bioprinter 10 comprises a sample loading system 20 for loading a sample 100 from a sample container 110 into a holding reservoir 120; a selector valve 30 in fluid communication with the holding reservoir 120 for directing the sample 100 into the holding reservoir 120; a droplet dispensing system 25 in fluid communication with the holding reservoir 120, the droplet dispensing system 25 adapted to print sample droplets 101 from the holding reservoir 120 onto a substrate 125; a control system 40 to control operation of the sample loading system 20, the selector valve 30, and the droplet dispensing system 40; a laminar air flow system 50; and a housing 60 encompassing the sample loading system 20, the selector valve 30, the droplet dispensing system 40 and the laminar air flow system 50.

Sample Loading System

Referring to FIGS. 1 to 4, the sample loading system 20 is adapted to access samples 100 contained in one or more sample containers 110 and is in fluid communication with one or more holding reservoirs 120. The holding reservoirs 120 are configured to hold samples 100 from the sample containers 110. The sample containers 110 can be a standard chromatography vial 111 having a cap 112 comprising a rubber septum 113 used in laboratories for storage and transport of samples. The vials 111 are typically manufactured from glass, plastic or any suitable material capable of maintaining a sterile environment within the vial 111. The vials 111 are made in multiple sizes to accommodate various samples 100, typically smaller vials storing approximately 5 ml and larger vials storing approximately 10 ml. The sample loading system 20 may comprise one sample container 110, or a plurality of sample containers 110, depending on the 3D cell construct to be printed by the bioprinter 10.

Each holding reservoir 120 is adapted to store a sample 100 received from one of the sample containers 110. Each holding reservoir 120 is manufactured from elongate tubing 122 wrapped inside a reservoir housing 121. The elongate tubing 122 may be coiled and encased in the housing 121. The elongate tubing 122 is a spool of flexible tubing 122. In certain embodiments, the flexible tubing 122 is made from Polytetrafluoroethylene (PTFE) tubing, or other suitable material such as fluorinated ethylene propylene (FEP), ethyltrifluoroethylene (ETFE), polyether ether ketone (PEEK), silicone, thermoplastic elastomer (TPE) or stainless steel. In alternative embodiments, each holding reservoir 120 is a container with an inlet, an outlet, and a storage cavity for storing a sample 100. The bioprinter 10 can include one or more holding reservoirs 120, corresponding to one or more individual and differing samples 100.

The sample 100 in each sample container 110 can be a cell suspension, water, ethanol, bio-ink, activator, cleaning solution, flushing fluid, cell culture media, or drug dispersed in solution, which are described in detail below. The sample 100 stored in the sample container 110 may or may not be sterile.

The sample loading system 20 comprises at least one needle 130 that is insertable into each sample vial 111 and is in fluid communication with the one or more holding reservoirs 120. In the embodiment depicted in the drawings, there is a single needle 130. The needle 130 is 50 mm long, bevel tip, 16 gauge, made from stainless steel. The needle 130 may be operatively associated with the sample loading system 20 for removing a sample 100 from each vial 111. The needle 130 is movable in the z-direction to insert the needle 130 into a vial 111 from above by a first positioning unit 140. The first positioning unit 140 is a miniature electric linear actuator 140a with a stroke of 60 mm driven by a lead screw 140b coupled to a stepper motor 140c, illustrated in FIG. 3 and FIG. 4.

The bioprinter 10 includes the flow selector valve 30 that directs a sample 100 taken from a sample container 110 to a holding reservoir 120. This is so that each sample 100 taken from each vial 111 is held in a separate holding reservoir 120 to separate each sample 100 to maintain sterile conditions.

The sample loading system 20 and droplet dispensing system 25 of the bioprinter 10 are connected by tubing 150. The tubing 150 is selected from a number of different materials, diameters and lengths, based on its desired location and functional requirements. The tubing 150 connecting the sample loading system 20 to each holding reservoir 120 is 2.16 mm inner diameter and 3.175 mm outer diameter PTFE tubing. The elongate tubing 122 in each holding reservoir 120 is ⅛" PTFE tubing.

To prime each holding reservoir 120 with a sample 100, the sample 100 is moved from a vial 111 to, and through, the selector valve 30 using a pump 160. The pump 160 may be a positive displacement pump such as a peristaltic, diaphragm or syringe pump. The pump 160 is connected to the selector valve 30 which comprises a suitable channel 31 for directing the sample 100 into the suitable (and isolated) holding reservoir 120. The valve 30 is a low pressure flow-through selector valve 30 manufactured by VICI Valco Instruments Co Inc. The flow selector valve 30 comprises many channels 31, such as 4, 6, 8, 10, 12 or 16 channels. The flow selector valve 30 has a common inlet connected to the pump 160 and needle 130. When a channel 31 is selected, the selected channel 31 is fluidically connected to the pump 160 and needle 130. When a channel 31 is not selected, that channel 31 is fluidically connected to pressurised air from an air pressure regulator 171 in the pressure regulator manifold 170. The pressure in each holding reservoir 120 or channel 31 is independently set by a respective regulator 171 in the regulator manifold 170. Each regulator 171 in the regulator manifold 170 is connected to the selector valve 30 using 4 mm Nylon tubing and ⅛" PTFE tubing. The number of pressure regulators 171 in the regulator manifold 170 is equivalent to the number of holding reservoirs 120 or channels 31. This allows the pressure to be set independently for each valve 252 of the droplet dispensing system 25, which means the bioprinter 10 may support a wide range of fluid viscosities in each valve 252.

The pressure regulators 171 in the regulator manifold 170 of the sample loading system 20 independently control pressure feeding into each channel 31 of the selector valve 30 and the holding reservoirs 120. The pressure regulator manifold 170 is operatively connected to a compressed air supply inlet 180 and a static pressure reservoir (not shown). The bioprinter 10 includes an air filter 190 within the housing 60 for filtering the air from the compressed air supply inlet 180. The pump 160 is operably coupled to the needle 130 for transferring a sample 100 in a sample container 110 to a holding reservoir 120. The pump 160 may be operably reversible for resuspension of the sample 100 in the sample container 110.

A seal 114 is formed by a rubber septa 113 of each sample container 110 and upon operation of the first positioning unit 140 is punctured using the needle 130 driven by the first positioning unit 140. The first positioning unit 140 is operated by a control system 40 and robotic linear actuators 140a. The control system 40 positions the first positioning unit 140 by moving a stepper motor 140c on the linear actuator 140a by a desired number of steps. The first positioning unit 140 is operably coupled to the needle 130 for positioning the needle 130 into puncturing-engagement with a sample container 110 and out of puncturing-engagement with the sample container 110. The channel 31 is selected on the selector valve 30, the micro-solenoid valve 252 is opened and the pump 160 is turned on to move the sample 100 from the sample vial 111, through the needle 130, tubing 150, pump 160, selector valve 30, and into a holding reservoir 120. The pump 160 is then turned off and the micro-solenoid valve 252 is closed. The channel 31 is deselected on the flow selector valve 30. The pressure is then set by the respective regulator 171 of the regulator manifold 170 and the micro-solenoid valve 252 is fired repeatedly until all air is out of the tubing line 150 and the sample 100 is fired from the holding reservoir 120. The above process is repeated to prime each holding reservoir 120 that is to be used.

The sample loading system 20 further comprises a second positioning unit 141 operably coupled to the needle 130 and the printhead 250 of the droplet dispensing unit 25, the second positioning unit 141 for positioning the needle 130 and the printhead 250 in two-dimensional space above the sample containers 110 and the substrate 125. The second positioning unit 141 is configured to move the needle 130 and the printhead 250 along a track 142. The second positioning unit 141 may be a 3-axis motion control stage unit. The second positioning unit 141 is a belt driven linear actuator 141a with a stroke of 300 mm. The belt 141b is a toothed belt and driven by a stepper motor 141c.

To print sample droplets 101, one or more holding reservoirs 120 and micro-solenoid valves 252 are primed as described above, and sample droplets 101 are fired from one or more nozzles 253 of a printhead 250 of the droplet dispensing system 25, and deposited on the substrate 125 in a predetermined manner controlled by computer-controlled software 40. This droplet dispensing system 25 is described in more detail below.

To clean the bioprinter 10, detergent can be moved from sample vials 111 using the needle 130 to and through the tubing lines 150, selector valve 30, the holding reservoir 120, using the sample loading system 20 as described above. Detergent is ejected from the nozzles 253 of the droplet dispensing system 25 into a waste container 205. This process is repeated for other cleaning chemicals, such as 70% ethanol and water. The cleaning of the bioprinter 10 is finished when all water has been flushed through the lines and only air is being ejected from the nozzles 253 of the droplet dispensing system 25, described in detail below.

To resuspend samples in the vials 111, the needle 130 can be moved towards the respective sample vial 111 using the first and second positioning units 140 and 141 until the needle 130 punctures the sample vial septa 113 and engages the sample 100. The cell-containing sample 100 in a sample vial 111 is moved from the sample vial 111, through the needle 130 and tubing 150 using the peristaltic pump 160. The cell-containing sample 100 is moved in the opposite direction (i.e. towards the sample vial 111) using the peristaltic pump 160 in reverse. This process of moving the cell-containing sample from and towards the vial 111 via the needle 130 and tubing can be repeated as desired.

Sample Tray

Figure 5:
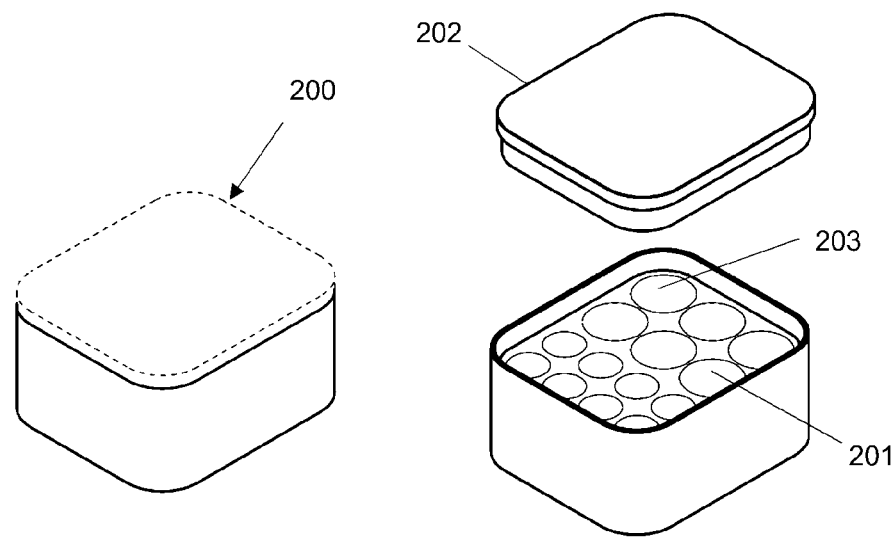
FIG. 5 is a perspective view of a removable sample tray used in the sample loading system.
Figure 6:
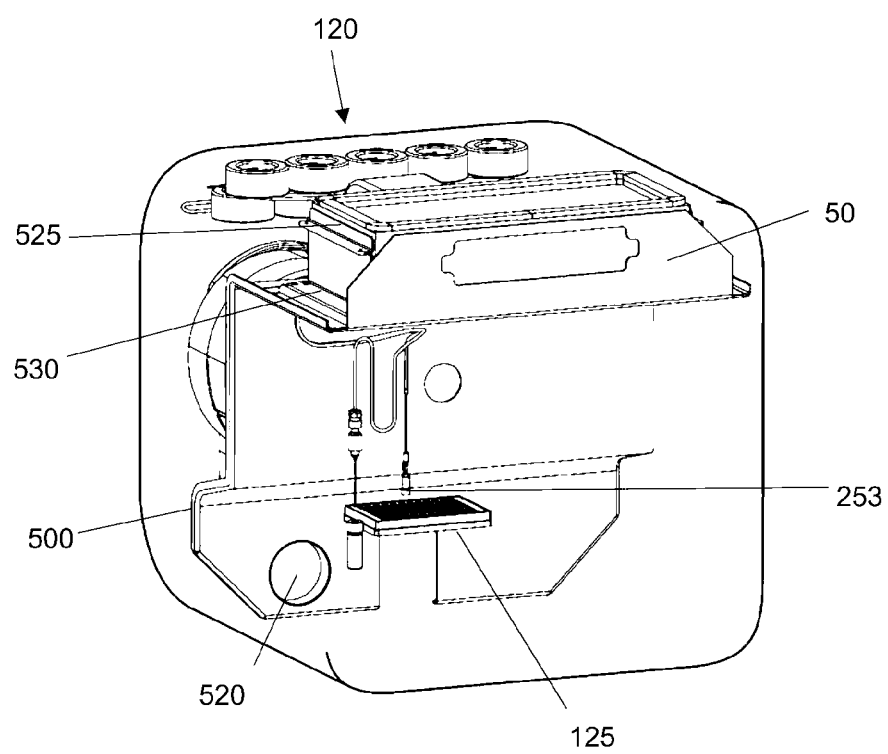
FIG. 6 is a front perspective view of the bioprinter with a laminar air flow system attached.
Figure 7:
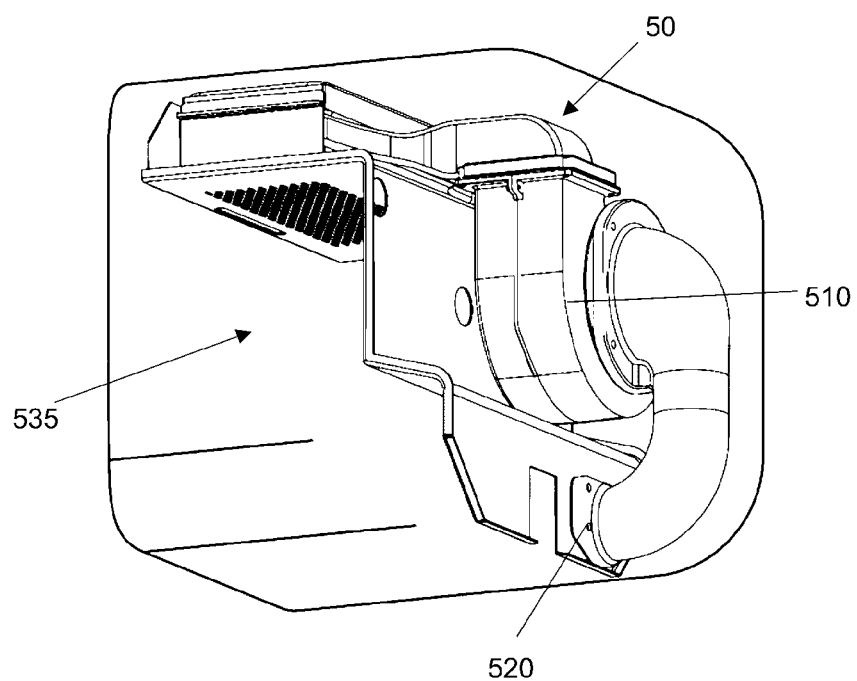
FIG. 7 is a rear perspective view of the bioprinter showing only the laminar air flow system.
Figure 8:
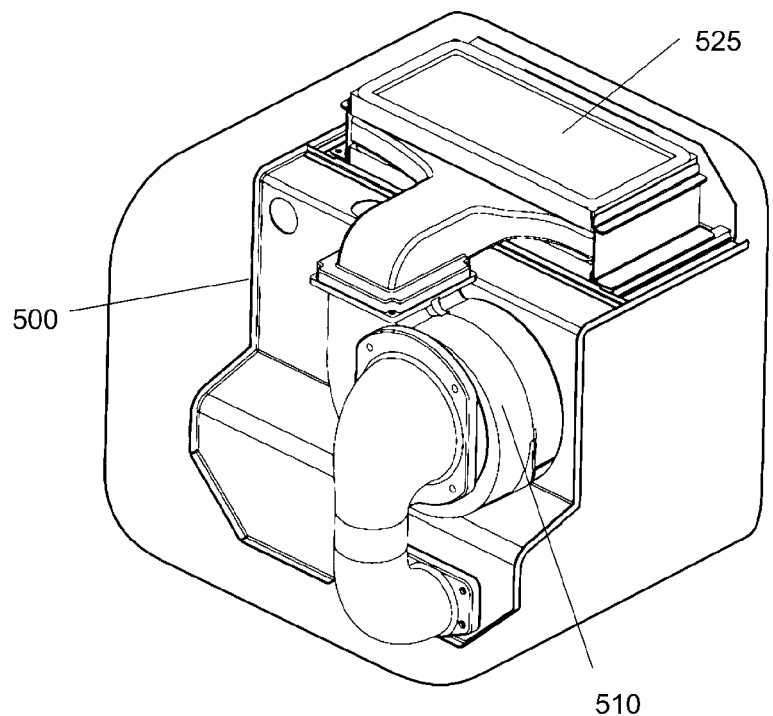
FIG. 8 is rear perspective view of the bioprinter showing only the laminar air flow system of FIG. 7.
Figure 9:
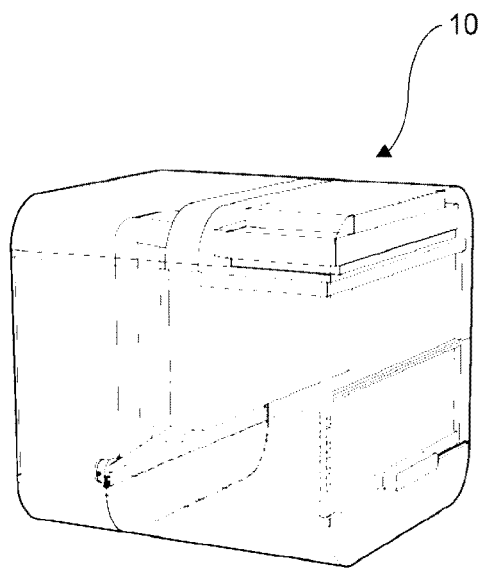
FIG. 9 and FIG. 10 show the bioprinter with clear panels illustrating the air flow path of the laminar air flow system.
Figure 10:
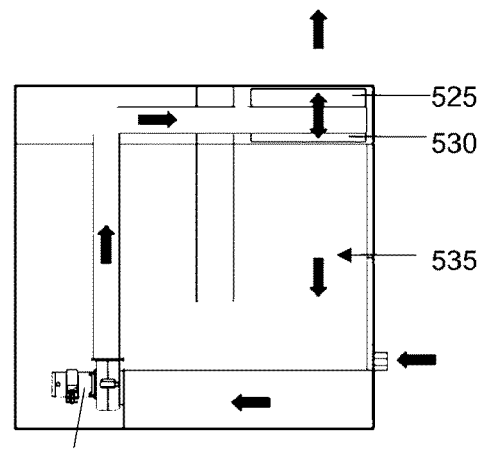
Figure 13:
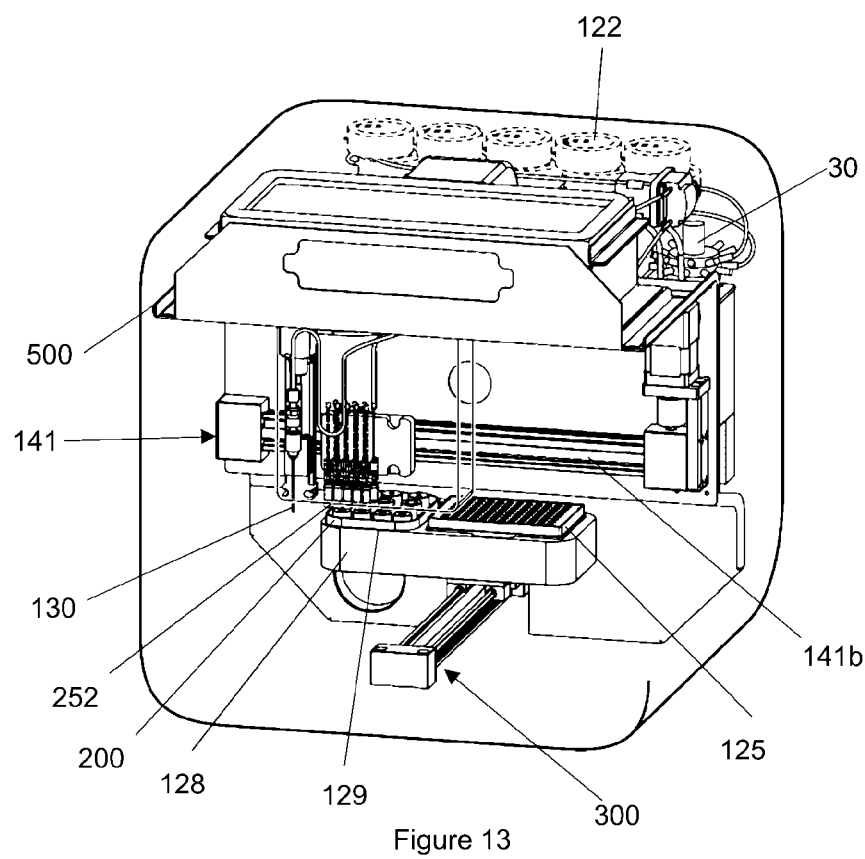
FIG. 13 is a front perspective view of the bioprinter of FIG. 11 with the laminar air flow system installed.
Figure 16:
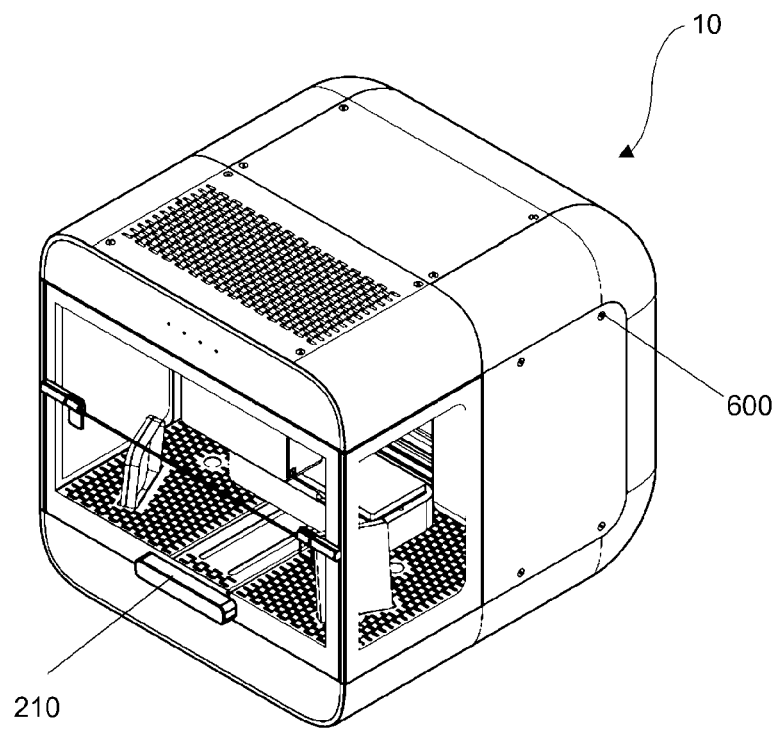
FIG. 16 is front perspective view of an assembled bioprinter.

The sample containers 110 may be housed in a removable sample tray 200 that may also be sterile. It is envisaged that up to 14 vials 111 can be housed in the removable sample tray 200, but any suitable number of vials 111 can be housed in the removable sample tray 200. The removable sample tray 200 has one or more sample container housings 201 adapted to store sample containers 110 of differing size, such as vials 111 and waste containers 205. The removable sample tray 200 as shown in FIG. 5 has a lid 202 and a tray 203. The removable sample tray 200 may be manufactured from plastic or other suitable material. The removable sample tray 200 is loadable into a recess 129 of the printstage 128 of the bioprinter 10 via the hinged door 210 as shown in FIGS. 13 and 16. In alternative embodiments, the sample containers 110 are loadable into the removable sample tray 200. The removable sample tray 200 provides a substantially sterile environment for storing the vials 111, as well as each vial 111 being sterile.

It is also envisaged that instead of the removable sample tray 200, the sample container housings 201 may be integral with printstage 128. In this case, each sample container 110 would be loadable into the printstage 128 via the hinged door 210 of the bioprinter 10.

The removable sample tray 200 housing the sample containers 110 may further include the waste container 205 for receiving waste when flushing the sample loading system 20. The removable tray 200 may further include a cleaning container 204 for cleaning the sample loading system 20, the selector valve 30, and droplet dispensing system 25.

Droplet Dispensing System

Referring to FIGS. 11 to 15, the droplet dispensing system 25 includes the printhead 250 operably coupled to the plurality of holding reservoirs 120 and adapted to dispense sample droplets 101 onto the substrate 125 from each holding reservoir 120. The at least one printhead 250 may be an array of valves 251. The array of valves 251 may comprise a plurality of micro-solenoid valves 252. The micro-solenoid valves 252 may be VHS Series Solenoid Valves manufactured by The Lee Company. Each micro-solenoid valve 252 includes a nozzle 253 with an orifice diameter of 0.003", 0.005" or 0.007". Each micro-solenoid valve 252 is opened by applying a spike and hold voltage across the solenoid coil. The spike voltage is 24V and the hold voltage is 5V. The duration of the spike voltage is between 0.2 and 0.5 ms. When the voltage is switched off the valve 252 returns to the closed position.

Each nozzle 253 may be a jeweled orifice dispensing nozzle 253 controlled by a microcontroller, namely the control system 40. The samples 100 are stored in the holding reservoirs 120 upstream of the micro-solenoid valves 252 and nozzle 253. The internal diameter of the jeweled orifice nozzles 253 can be between 127 and 254 µm depending on the fluid viscosity and the desired droplet volume of the sample droplet 101.

The droplet dispensing system 25 includes the compressed air supply inlet 180, operably coupled to the pressure regulator manifold 170 via air filter 190. The air moves the samples 100 around the sample loading system 20 and droplet dispensing system 25, so as to be dispensed via the nozzles 253 of the printhead 250. The desired sample droplet 101 volume can also be adjusted using the backpressure set by the pressure regulators 171 of the regulator manifold 170 and the open time of the respective valves 252 open time. Typically, the backpressure is set to a pressure between 1 and 60 psi, the valve 251 open time is 0.3 ms or greater and the droplet volume is between 1 and 500 nl.

The droplet dispensing system 25 may further comprise a third positioning unit 300 operably coupled to the printstage 128, the third positioning unit 300 for positioning the printstage 128 in two-dimensional space. The third positioning unit 300 is configured to move the printstage 128 along a track 301. The track 142 extends perpendicularly to the track 301. Referring to FIG. 13, the printstage 128 supports the substrate 125 and has a recess 129 that is configured to removably receive the sample tray 200. The 3-axis motion control stage is capable of accurately positioning the droplet dispensing system at a resolution of 10 µm in all three (X, Y and Z) dimensions.

In a sterile environment, each of the activator, bio-ink and bio-ink or cell-ink containing cells (ie, samples 100) are slowly loaded into the appropriate holding reservoir 120 using the sample loading system 20 to avoid the generation of small bubbles.

The bioprinter is equipped with a power supply in the form of a 24V DC power supply (not shown).

The compressed air supply inlet 180 is supplied from an air compressor (not shown). The air compressor can supply an air pressure between 3 and 10 bar. The compressed air can be supplied from a common compressed air line that is common in research laboratories.

Tubing 150 within the droplet dispensing system 25 is 40 mm 1/16" Teflon tubing. This tubing 150 connects the holding reservoirs 120 to the array of valves 251 of the printhead 250.

The sample loading system 20 can automatically load samples 100 into the holding reservoirs 120 for printing. The system has several advantages over current state of the art bioprinting systems. Firstly, bio-inks can be stored in easy to handle sample containers 110 such as glass or plastic vials 111. These samples containers 110 are easily sterilized before filling with bio-ink samples. End users, such as biologists, deposit their cells inside the appropriate vial 111 using the usual methods, for example a pipette. Depositing cells inside the bio-ink vials 111 can be carried out inside a bio-safety cabinet to ensure samples 100 are not contaminated. After depositing cells, the vials 111 can be placed inside the bioprinter 10 in the appropriate location.

The sample loading system 20 allows bio-inks and bio-inks containing cells to be loaded from individual vials 111 sealed with rubber septa 113. This is achieved using the needle 130 that is positioned using the z-axis linear actuator 140. The needle 130 is fluidically connected to the positive displacement pump 160. When the tip of the needle 130 pierces the septa 113 and is positioned inside the vial 111, the pump 160 is engaged and fluid sample 100 is pumped out of the vial 111.

The printhead 250 may comprise multiple electronic pressure regulators 171 that are individually adjustable for printing a large range of viscosities, droplet sizes etc, based on user input, the sample construct, and/or the desired cell construct. The electronic pressure regulators 171 are operably connected to the array of valves 251.

Figure 11:
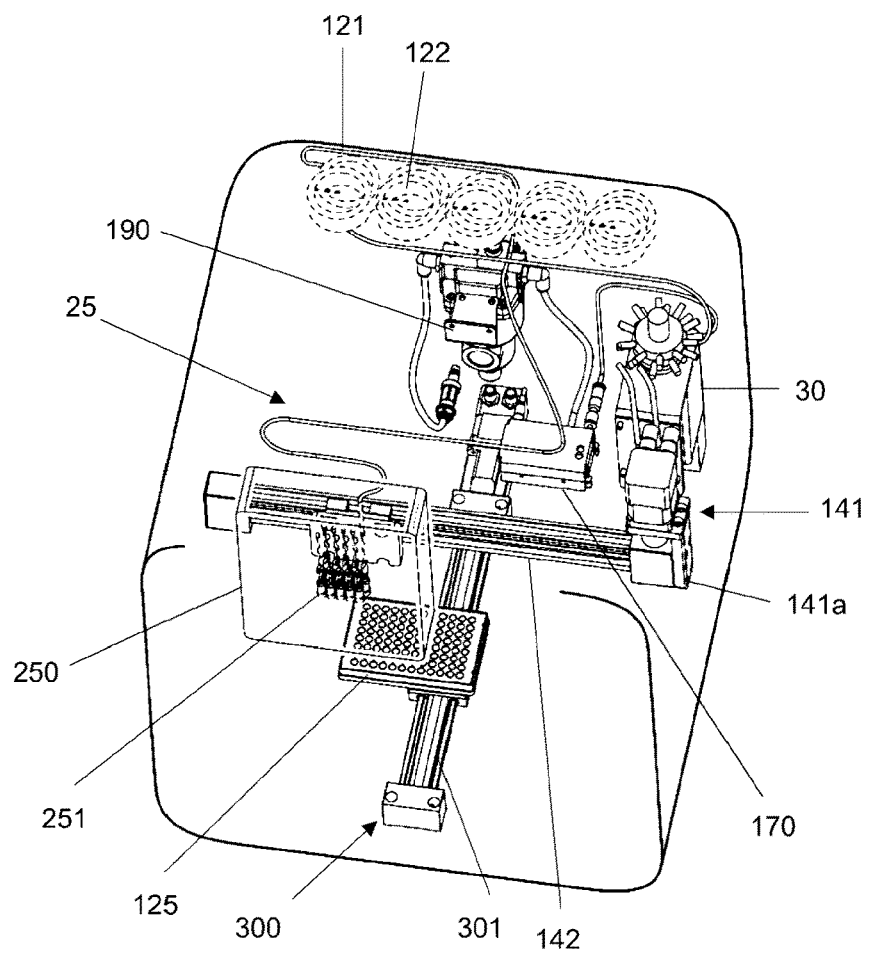
FIG. 11 is a top perspective view of the bioprinter with the positioning units for the droplet dispensing system and sample loading system illustrated.
Figure 12:
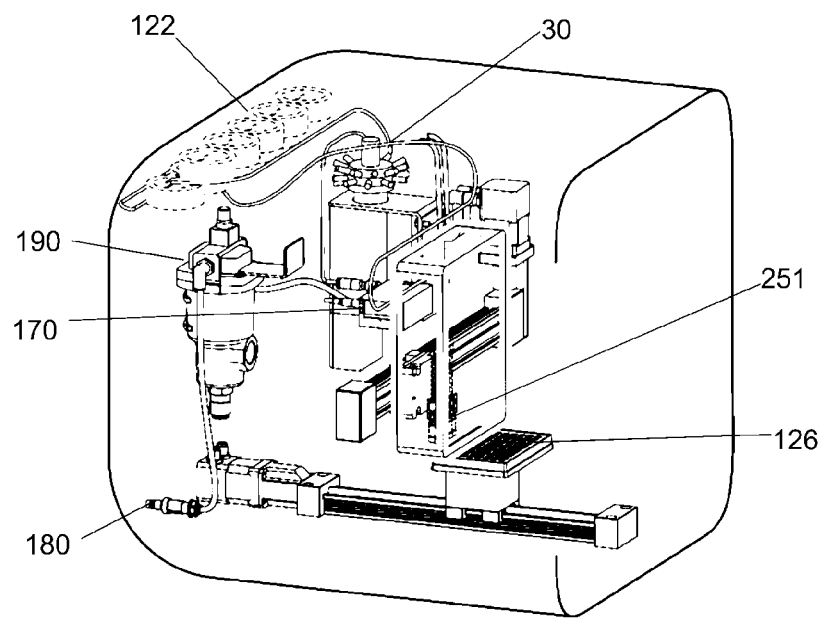
FIG. 12 is side perspective view of the bioprinter with a plurality of holding reservoirs and the compressed air supply system.
Figure 14:
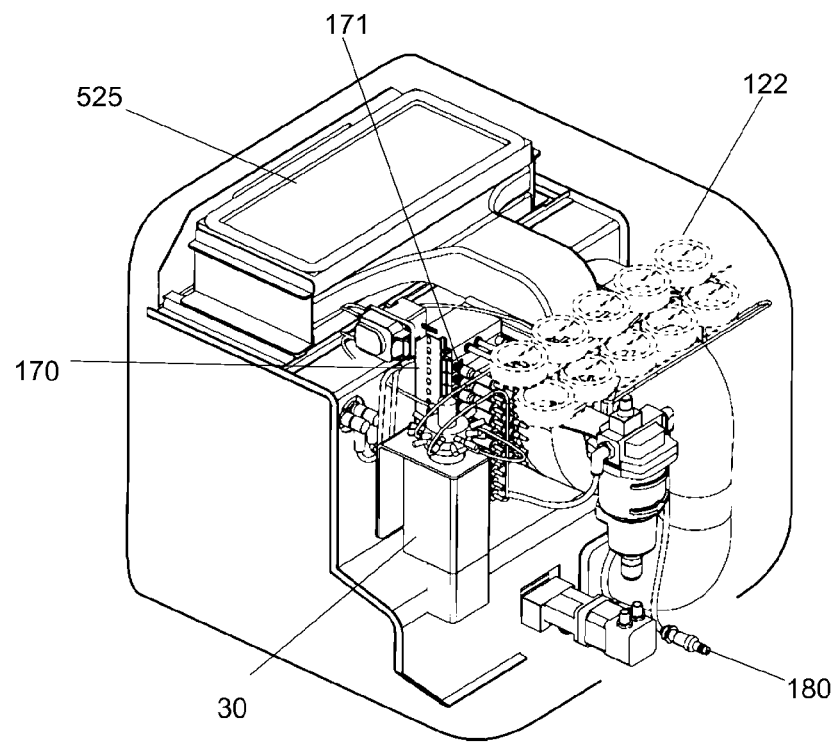
FIG. 14 is a rear perspective view of the bioprinter of FIG. 13.
Figure 15:
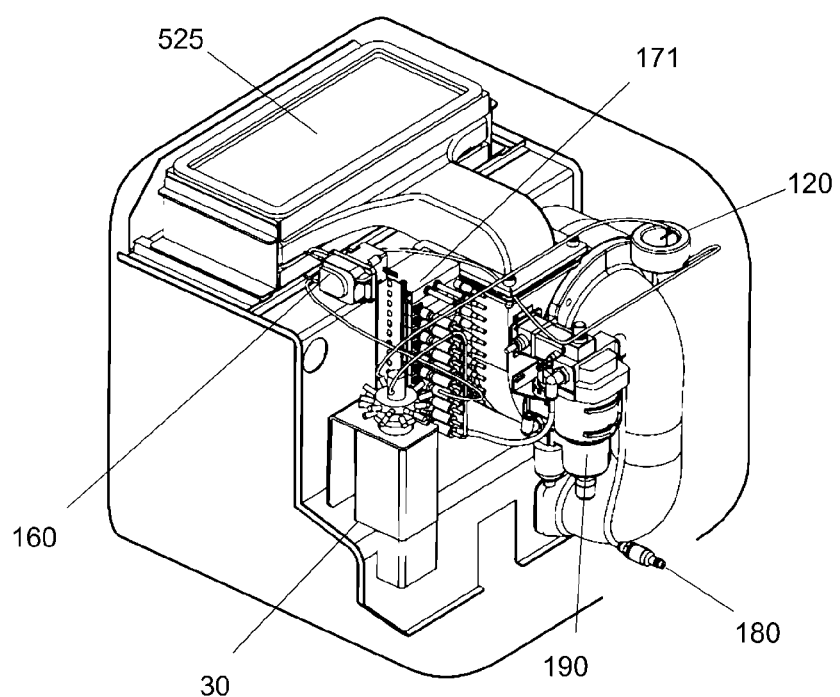
FIG. 15 is a rear perspective view of the bioprinter with a single holding reservoir.

The bank of pressure regulators 171 (it is envisaged that the bioprinter 10 may include 10, as there are up to 10 holding reservoirs 120) is contained in the pressure regulator manifold 170. The function of the manifold 170 is to distribute pressurised air from the external air compressor connected to the supply inlet 180 to each of the regulators 171. In FIG. 11 and FIG. 12, only a single regulator 171 and one side of the manifold 170 is shown. In FIG. 14 and FIG. 15, a bank of ten regulators 171 is shown.

An exemplary embodiment of the sample loading system of the bioprinter 10 comprises the steps for loading samples 100 into the holding reservoir 120 as follows:
1. Move Selector Valve 30 to selected channel 31;
2. Open micro-solenoid valve 252;
3. Position needle 130 above vial 111 using x-axis and y-axis actuators;
4. Lower needle 130 into vial 111 piercing the vial septum 113 using z-axis actuator;
5. Engage peristaltic pump 160;
6. Pump fluid from vial 111 through selector valve 30 into tubing holding reservoir 120;
7. Stop pump 160 when fluid reaches nozzle of micro-solenoid valve 252; and
8. Close micro-solenoid valve 252.

Another exemplary embodiment of the sample loading system 20 of the bioprinter 10, in particular the steps for cleaning and sterilising comprises the following steps:
1. Position micro-solenoid valve 252 over waste spittoon or vial;
2. Empty any fluid remaining after print job into waste container 205;
3. Move Selector Valve 30 to selected channel for cleaning;
4. Position needle 130 above vial 111 containing ethanol using x-axis and y-axis actuators;
5. Lower needle 130 into vial 111 piercing the vial septum using z-axis actuator;
6. Open micro-solenoid valve 252;
7. Engage peristaltic pump;
8. Pump ethanol from vial 111 through selector valve 30 and open micro-solenoid valve 252;
9. Stop pump when sufficient ethanol has passed through open micro-solenoid valve 252;
10. Close micro-solenoid valve 252;
11. Repeat process with detergent; and
12. Repeat the process with water.

Figure 20:
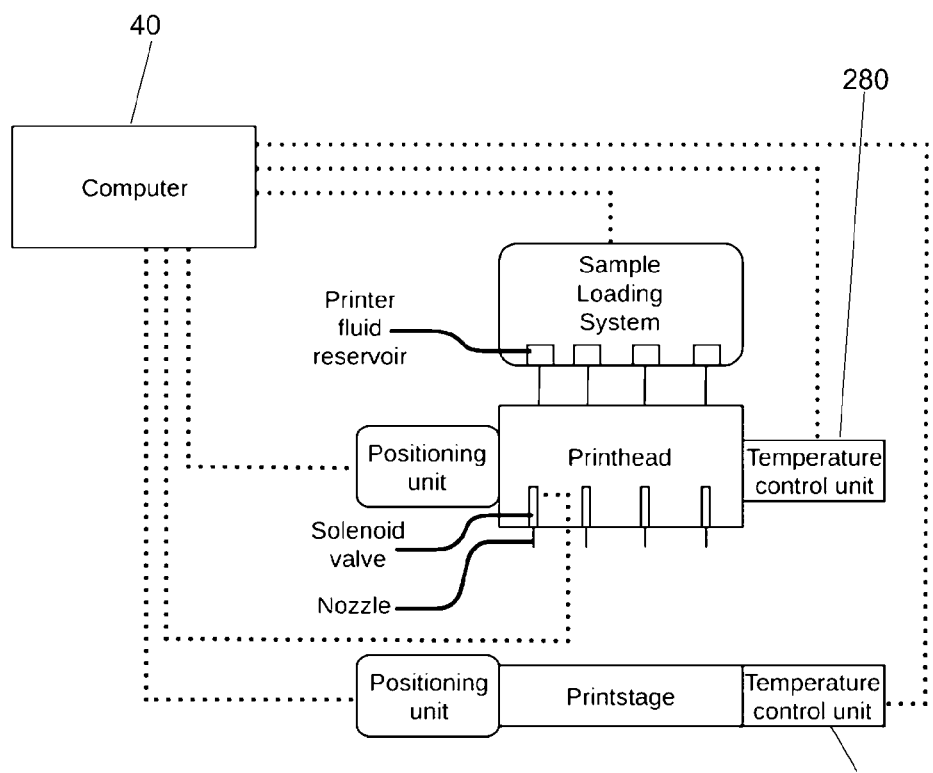
FIG. 20 is a flow chart schematic of the bioprinter operatively associated to a control system computer.

The bioprinter 10 is adapted to print onto many kinds of substrate 125, such as micro-well plates and Petri dishes. Referring to FIG. 20, the substrate 125 can be heated to 37° C. to assist cell proliferation using a temperature control unit 280. Both the temperature control units 280 regulate the temperature inside the bioprinter 10, based on the need of the 3D cell construct conditions necessary for optimal growth conditions. The temperature control units 280 are adjustable to between 36° C. and 38° C. to regulate the temperature of the printhead 250, the substrate 125 disposed on the printstage 128, and/or the interior of the bioprinter 10.

The substrate 125 that is disposed on and supported by the printstage may be a multi-well plate 126. The substrate 125 may be biocompatible consumables used to enclose and culture the printed cellular structure. These substrates may include:
  Microtitre plate of different well configurations (6, 12, 24, 48, 96 and 384-well);
  Microtitre plate with coverslip bottom of different well configurations (6, 12, 24, 48, 96 and 384-well);
  Coverslips and microscope slides;
  Fluorodish of various sizes; and
  Chamber slides of different chamber configurations (1, 2, 4, 8 and 16).

To clean the tubing lines 150, array of valves 251 and the nozzles 253, detergent can be moved from sample vials 111 to, and through the valves 252 and the nozzles 253 using the droplet dispensing system 25 as described above. Detergent is ejected from the nozzles 253 into the waste container 205. This process is repeated for other cleaning chemicals, such as 70% ethanol and water. The cleaning of the tubing lines 150 and the printhead 250 is finished when all water has been flushed through the lines 150, the array of valves 251 and the nozzles 253 and only air is being ejected from the nozzles 253.

Laminar Flow System

Referring to FIGS. 6 to 10, the bioprinter 10 further includes a laminar flow system 50 as illustrated in FIGS. 6 to 10. Sterility and operator safety is a major concern in 3D bioprinting applications. It is normally achieved by locating the bioprinter inside a biosafety cabinet or clean room. Typically, biosafety cabinets and clean rooms are regarded as precious and expensive space in a tissue culture lab.

Therefore, there is a need for solutions to minimise use of bio-safety cabinet and clean room space in 3D bio-printing applications.

The integrated laminar flow system 50, integrated into the bio-printer 10, provides the sterile environment for bio-printing of cells and 3D tissue culture models without requiring biosafety cabinet or clean room facilities. Furthermore, the operator is protected using directional airflow to draw air from the outside environment through the front access.

Figure 21:
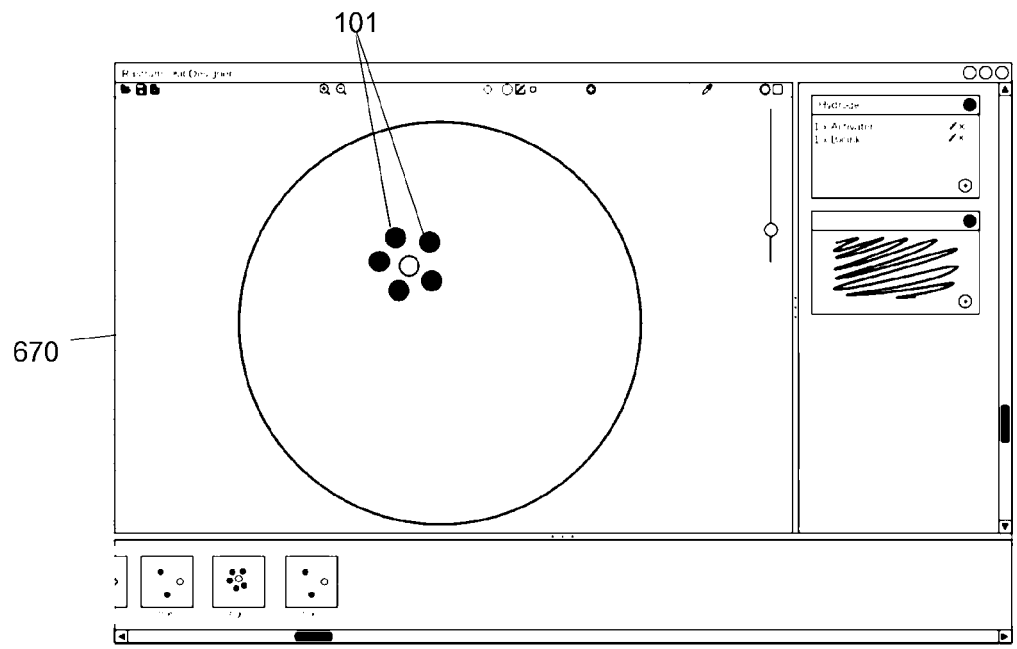
FIG. 21 is an exemplary graphical user interface of the control system software implemented on the computer showing the 3D cell construct design.

The laminar air flow system 50 includes a chamber or enclosure with a metallic frame 500, for example stainless steel, and is provided with a metallic grate at the base to allow contaminated airflow to be drawn into to the electrically powered blower fan or centrifugal fan 510. The contaminated air is pumped through a duct inlet 520 using the fan 510 and into a positive pressure chamber 535 consisting of two High-Efficiency Particulate Arresting (HEPA) filters 525 and 530. The HEPA filters 525 and 530 may remove at least 99% of particles from the contaminated air flow. One HEPA filter 525 acts as an exhaust to the external environment and the other HEPA filter 530 recycles the air flow to the sterile chamber 535. It is envisaged that each filter will take approximately 50% of the airflow. FIG. 21 illustrates the air flow into the bioprinter 10, through the duct inlet 520 via the blower fan 510, through the HEPA filters 525 and 530 and either exhausted out or recycled. The airflow from the recycle HEPA filter 525 to the sterile chamber 535 provides unidirectional downward airflow to the sterile chamber 535 with a typical velocity of 0.45 m/s. This airflow provides a uniform clean airflow over the bio-printed sample droplet 101 significantly reducing the risk of particle contamination in the sample 100.

During a bio-printing operation, the front access hinged door 210 must be closed to reduce the risk of particle contamination. Therefore, the blower fan 510 flow rate can be reduced by decreasing the blower rpm. The reduced airflow in the sterile chamber 535 reduces the effect of dehydration on the printhead 250 and sample 100. In addition, it reduces the effect of the airflow disturbing sample droplets 101 during their flight from the printhead 250 to the printing substrate 125.

Control Software

The bioprinter 10 is controlled via custom software developed for printing biological assays. The control system 40 comprises the control software that includes a non-transitory computer readable medium having the programmed instructions for operating the bioprinter 10. The non-transitory computer readable medium is located separately from the bioprinter 10 and is operatively connectable to the bioprinter 10.

Figure 22:
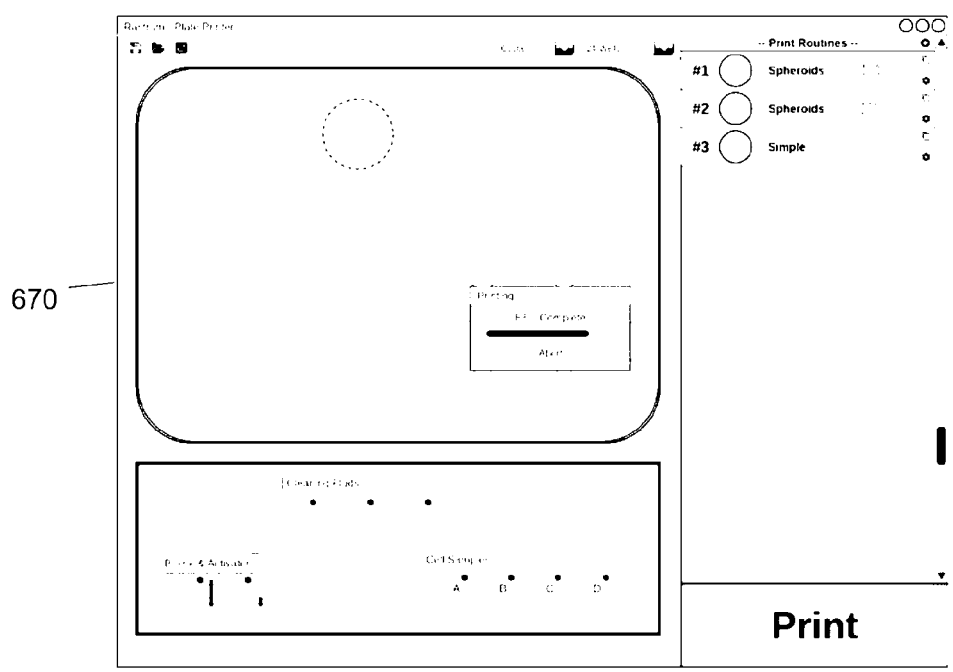
FIG. 22 is an exemplary graphical user interface of the control system software implemented on the computer showing printing of the 3D cell construct in a multi-well plate.
Figure 23:
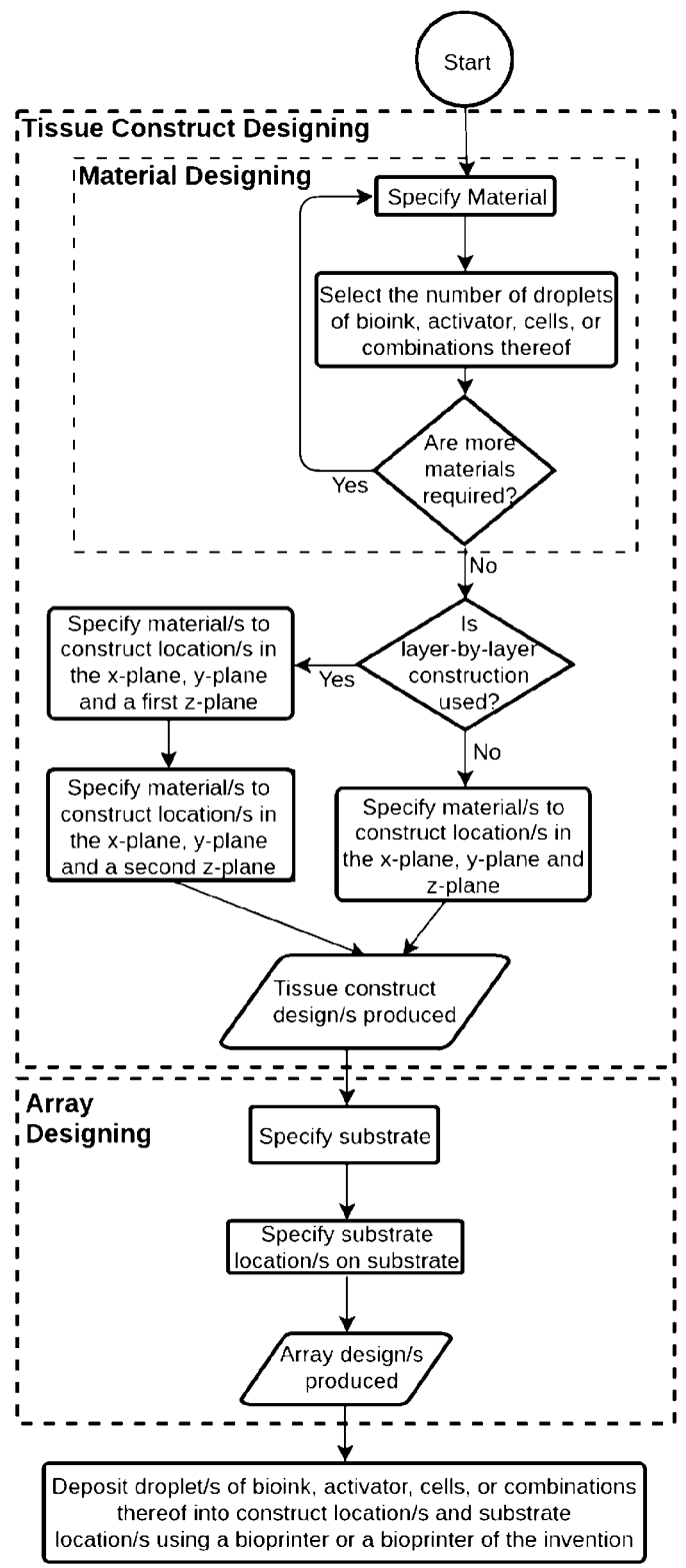
FIG. 23 is a flow chart schematic of designing the 3D cell construct integrated with the bioprinter.

The software includes a graphical user interface (GUI) as illustrated in FIG. 21 and FIG. 22. Through the GUI, the end user can select different assay printing routines and change the assay parameters, such as droplet spacing and droplet volume. The user can also manually control the spatial position of the droplet dispensing system and create a custom pattern of droplets. Additional features of the software include routines for cleaning, priming and purging of the droplet dispensing system.

Bioprinting requires a 3D model of the object to be printed. For tissue engineering applications, this is typically created using engineering tools such as CAD/CAM software. These tools are expensive and have a high degree of complexity, forcing scientists to spend time and resources learning engineering tools. For 3D tissue culture applications, the complexity of the structure to be printed is lower. There is need for a simple and intuitive method to create 3D structures for bio-printing in 3D tissue culture applications.

The software provided with the bioprinter 10 provides a method to design each layer of the 3D structure to be printed. In an embodiment, a grid is provided for the user to draw a pattern for each layer of the structure. The material to be printed can be defined as a mixture of multiple materials that are dispensed from different nozzles 253 in the printhead 250. For example, hydrogel can be defined a droplet of bio-ink mixed with a droplet of activator.

Typical substrates used in biology labs for tissue culture are multi-well plates such as 6, 12, 24, 48, 96 and 384-well plates. In an embodiment, an interface 670 is provided to print a previously defined 3D structures inside each well on a multi-well plate. The user firstly selects a well or arrays of wells and then selects the print routine to be printed in those wells.

The custom software provides the user interface for the user to input where in the array the user would like to bioprint a layer of the 3D cell construct. A print preview button 671 is provided with the software prior to printing to allow the user to visualise where the cells are being printed and what the construct will look like. A feature of the software is that it can control the bioprinter droplet size to change how the cell construct is printed. The intention behind the layering of the cell construct is to mimic how biologists use z stack layering in a microscope.

Generally, the bioprinter 10 will print 20-25 layers when building the 3D cell construct, but the number of layers is controlled using the control system and associated control software.

The positioning unit 141 coupled to the printhead 250, controlled by computer-controlled software, spatially-positioned the valves 251 and nozzles 253 during each ejection of sample droplets 101 of bio-ink, activator, cells, cell-ink, or combinations thereof. The computer-controlled spatial-positioning of the solenoid valves and nozzles, and computer-controlled droplet ejection from the valves 251 and nozzles 253 facilitate the generation of the 3D tissue construct.

To generate an array of 3D tissue constructs, the process of generating 3D tissue constructs was repeated at multiple locations on the substrate 125.

The control system records the identity of each sample 100 in the sample containers 110 by either user input or automatic recording. The intention is to know which sample containers 110 contain which sample 100, so that during printing, when the holding reservoirs 120 are storing their respective samples, the requisite sample is printed to the desired location.

Bioprinter Housing

Figure 17:
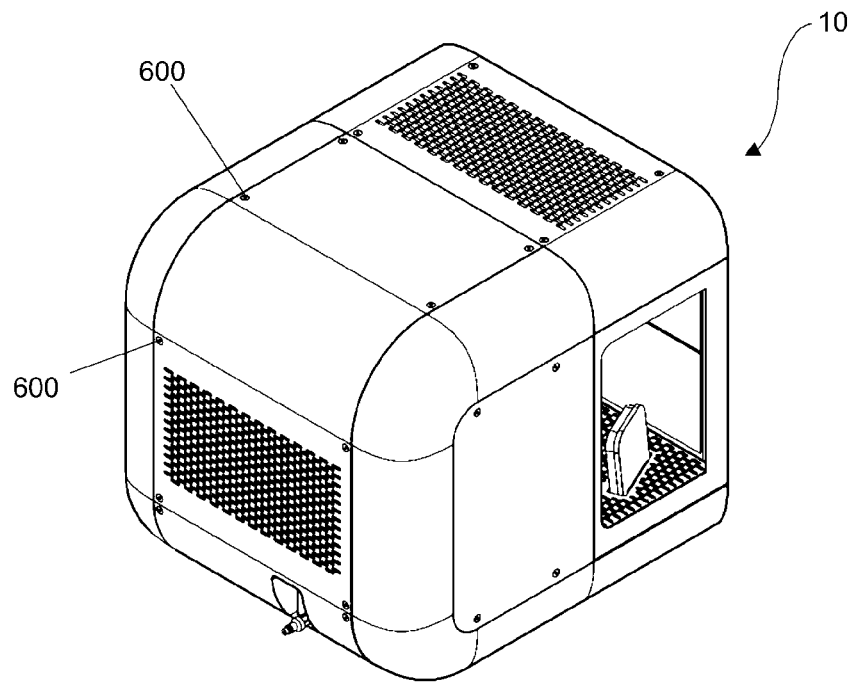
FIG. 17 is a rear perspective view of the bioprinter of FIG. 16.
Figure 18:
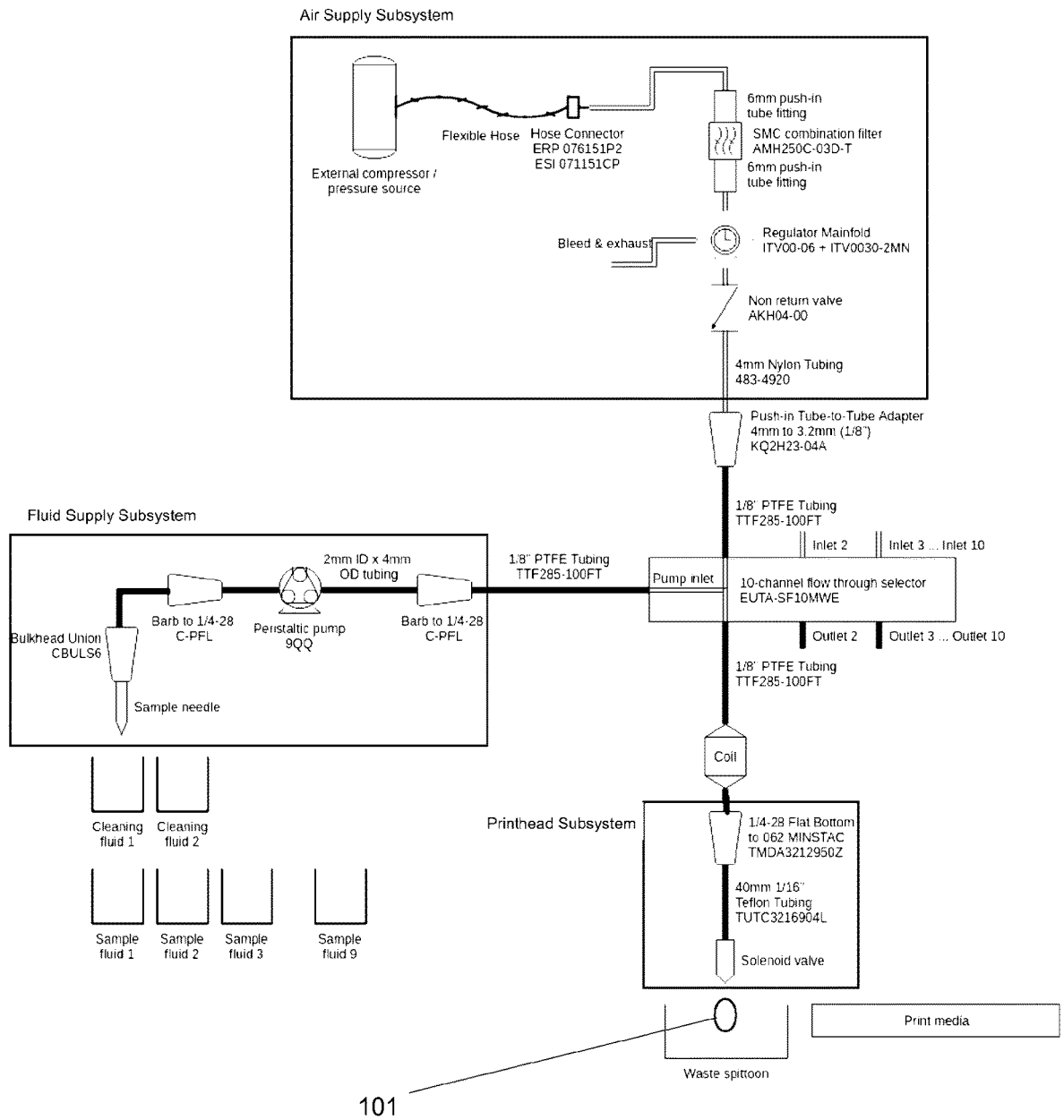
FIG. 18 is a flow chart schematic of the components bioprinter.
Figure 19:
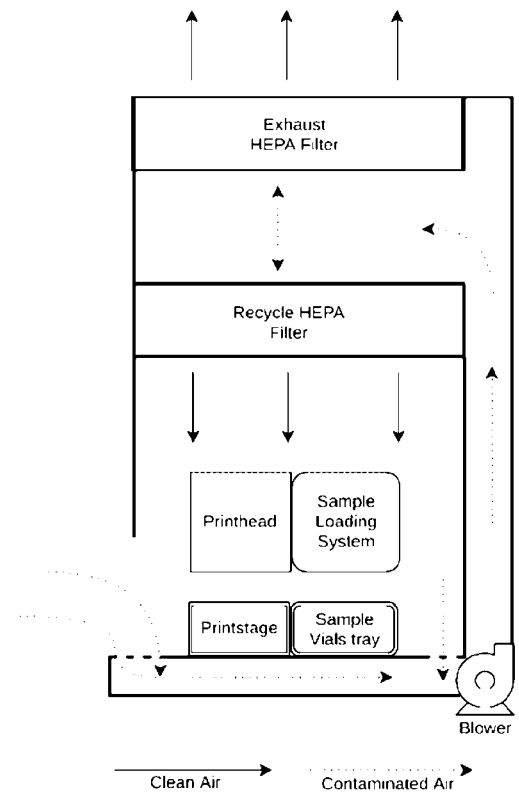
FIG. 19 is a side view of each component of the bioprinter showing the air flow path between the components of the laminar air flow system.

The bioprinter 10 comprises a housing 60 encompassing the sample loading system 20, the droplet dispensing system 25 and the laminar air flow system 50. The housing 60 is assembled from numerous panels made from steel, aluminum and stainless steel and assembled using screw fasteners 600. The housing 60 further includes the hinged door 210 in the front face, to allow access to the sterile chamber 535 of the bioprinter 10 by a user. The removable sample tray 200 is loadable into the bioprinter 10 via the door 210. The front panel and hinged door 210 can be made from glass or clear plastic. FIG. 16 and FIG. 17 illustrate the bioprinter assembly 10.

Method

In operation, the bioprinter 10 has the following steps for transferring the sample from the sample container to the holding reservoir ready to be utilised by the printhead for bioprinting 3D cell constructs. To prime the printer holding reservoirs 120 and solenoid valves with fluid, fluid is moved from sample containers to, and through, the solenoid valves using the sample loading system. The suitable channel is selected on the flow selector valve. The seal of a sample vial is punctured using the needle 130, the solenoid valve is opened. The peristaltic pump is turned on to move the desired amount of fluid from the sample container, through the needle, tubing, pump, tubing, flow selector valve, and into the holding reservoir. The peristaltic pump is turned off and the solenoid valve is closed. The suitable channel is deselected on the flow selector valve. The pressure is set by the regulator 171 and the solenoid valve 252 is fired repeatedly until all air is out of the line and droplet/s bio-ink, activator, cells, cell-ink, or combinations thereof are fired from the nozzle 253. The above process is repeated for each printer fluid reservoir and solenoid valve that is used.

Steps for loading bio-ink into holding reservoir:
1. Move Selector Valve to selected channel;
2. Open solenoid valve;
3. Position needle above vial using x-axis and y-axis actuators;
4. Lower needle into vial piercing the vial septum using z-axis actuator;
5. Engage peristaltic pump;
6. Pump fluid from vial through selector valve into tubing holding reservoir;
7. Stop pump when fluid reached nozzle of solenoid valve; and
8. Close solenoid valve.

To print bio-ink, activator, cells, cell-ink, or combinations thereof from the solenoid valves, printer fluid reservoirs and solenoid valves are primed as described above, droplets of bio-ink, activator, cells, cell-ink, or combinations are fired from the nozzles and deposited on the substrate in a predetermined manner controlled by computer-controlled software.

A positioning unit is coupled to the printhead 250, controlled by computer-controlled software, spatially-positioned the solenoid valves and nozzles during each ejection of droplets of bio-ink, activator, cells, cell-ink, or combinations thereof. The computer-controlled spatial-positioning of the solenoid valves and nozzles, and computer-controlled droplet ejection from the solenoid valves and nozzles facilitate the generation of the 3D tissue construct.

To generate an array of 3D tissue constructs, the process of generating 3D tissue constructs is repeated at multiple locations on the substrate.

Bio-Ink

In the present specification, bio-ink is defined as an aqueous solution of one or more types of macromolecule in which cells may be suspended or housed. Upon activation or crosslinking, it creates a hydrogel structure having its physical and chemical properties defined by chemical and physical composition of the bio-ink. Macromolecules are defined as an array of both synthetic and natural polymers, proteins and peptides. Macromolecules may be in their native state or chemically modified with amine or thiol-reactive functionalities.

Synthetic macromolecules may include:
Polysaccharides, such as polymers containing fructose, sucrose or glucose functionalities;
Non-ionic polymers, such as poly(ethylene glycol) (PEG), poly(hydroxyethyl methacrylate (PHEMA), poly(ε-caprolactone) (PCL), poly(vinyl alcohol) (PVA), poly(vinylpyrrolidone) (PVP), poly (NIPAAM) and poly(propylene fumarate) (PPF) and derivatives;
Polyelectrolytes—polymers that carry either positive or negative charge, amphoteric as well as zwitterionic polymer;
Polypeptides—a single linear chain of many amino acids (a minimum of 2 amino acids), held together by amide bonds; and
Nucleobase containing synthetic polymers—polymers with nucleobase (adenine, thymine, guanine or cytosine) repeating units.

Natural macromolecules may include:
Polysaccharides, such as alginate, chitosan, gellan gum, hyaluronic acid, agarose and glycosaminoglycan;
Proteins, such as gelatin, fibrin and collagen;
DNA and Oligonucleotides, such as single stranded DNA (ssDNA), double stranded DNA (dsDNA) DNAzymes and Aptamers; and
Basement membrane extracts.

Amine-reactive functionalities may include: aldehyde, epoxy, N-hydroxysuccinimide (NHS) and 2-vinyl-4,4-dimethylazlactone (VDM).

Thiol-reactive functionalities may include: alkenes, alkynes, azides, halogens and cyanates.

The bio-ink used and found suitable was alginate (at 2 w/v %) dissolved in calcium free DMEM supplemented with 10 v/v % FCS, L-glutamine and sodium pyruvate.

Bio-ink with dispersed SK-N-BE(2) neuroblastoma cells is referred to as bio-ink containing cells.

Activator

Activator is an aqueous solution comprising of either small molecules or macromolecules which interact with the bio-ink to form a hydrogel structure. The composition of the activator can be altered to control the physical properties of the resulting hydrogel. The type of activator used is highly dependent on the macromolecules used as well as the intended crosslinking process.

Activators can be selected from:
Inorganic salts such as calcium carbonate, calcium chloride, sodium chloride, magnesium sulphate. sodium hydroxide and barium chloride;
Photoinitiators such as 2,2-dimethoxy-2-phenylacetophenone (DMPA) and Irgacure;
Polyelectrolytes—polymers that carry an opposite charge to the macromolecules in the bio-ink. It could be cationic, anionic, amphoteric and zwitterionic;
Polypeptides—a single linear chain of many amino acids (a minimum of 2 amino acids), held together by amide bonds;
DNA linker—macromolecules carrying nucleotides or DNA sequences which complement those present on the bio-ink's macromolecules; and
Natural or synthetic macromolecules carrying amine or thiol groups, either natively or through chemical modifications.

The activator used for the alginate bio-ink was calcium chloride at 4 w/v % dissolved in MilliQ water.

Crosslinking or Gelation

This is the process whereby individual macromolecular chains are linked together by the activator to form a hydrogel. The crosslinking process can be classified to either chemical or physical crosslinking. Physical crosslinking or non-covalent crosslinking may include:
Ionic crosslinking—crosslinking via the interaction of the opposite charges present in the macromolecule and the activator. The activator may include charged oligomers, ionic salt and ionic molecule;

Hydrogen bonds—crosslinking via the electrostatic attractions of polar molecules. In this case, the macromolecule and the activator are carrying polar functionalities;

Temperature crosslinking—crosslinking via the rearrangement of the macromolecular chains as a response to change in temperature (heating or cooling); and Hydrophobic interaction or van der Waals force.

Chemical or covalent crosslinking involves chemical reactions between the macromolecule and the activator. The type of reactions may include:

Photocrosslinking whereby the crosslinking reaction is promoted by UV or light irradiation;

Michael-type addition reaction between thiols and vinyl-carrying macromolecules in aqueous media;

Schiff base reaction between amino and aldehyde groups;

Diels-alder reaction;

Click chemistry;

Aminolysis reaction to active ester group; and

Enzyme crosslinking.

Examples of other bio-ink and activator combinations are set out in the Table below:

| Bio-Ink | Activator |
| --- | --- |
| Positively charged polyelectrolyte (e.g. poly(trimethylammonium) or poly(guanidium) | Negatively charged polyelectrolyte (e.g. poly(sulfonate), poly(carboxylic acid) |
| Fluorenylmethoxycarbonyl (Fmoc) polypeptide | Phosphate buffer solution Cell culture medium |
| Thiol-reactive macromolecules (e.g. PEG-diacrylate, hyaluronic acid maleimide) | Photoinitiator and/or thiol-containing macromolecules (e.g. bis-thiol-PEG) Thiol-containing polypeptides (e.g. bis-cysteine functionalised peptide) |
| Amine-reactive macromolecules (e.g. PEG-co-Poly(benzaldehyde), aldehyde-alginate | Amine-containing polypeptides (e.g. bis-amine functionalised peptide, gelatin, collagen) |
| Charged polysaccharides (e.g. alginate and gellan gum) | Inorganic salts (e.g. calcium chloride, barium chloride). |
| Macromolecules containing nucleobase (e.g. Adenine) | Macromolecules containing the corresponding nucleobase pair (e.g. Thymine) |

Cell-Ink

Cell-ink is an aqueous solution of one or more type of molecules or macromolecules in which cells are to be and remain evenly suspended throughout the 3D bio-printing process. The concentration of the cell-ink is optimised to prevent cells from settling but still maintains high cell viability.

Cell-link can be selected from:

Small molecules such as glycerol; and

Macromolecules such as Ficoll™, dextran, alginate, gellan gum, methylcellulose and poly(vinylpyrrolidone) (PVP).

Ficoll™ is a neutral, highly branched, high-mass, hydrophilic polysaccharide which dissolves readily in aqueous solutions. Ficoll™ radii range from 2-7 nm and is prepared by reaction of the polysaccharide with epichlorohydrin. Ficoll™ is a registered trademark owned by GE Healthcare companies.

The cell-ink used was Ficoll™ 400 (at 10 w/v %) dissolved in PBS.

Cell-ink with dispersed SK-N-BE(2) neuroblastoma cells is referred to as cell-ink containing cells.

Gellan gum is a water-soluble anionic polysaccharide produced by the bacterium *Sphingomonas elodea* (formerly *Pseudomonas elodea*).

Cell-Culture Solutions

Cell-culture solutions are liquids that come into contact with the cultured cells and are suitable for various cell-related works. The preparation process includes careful analysis of the salt and pH balance, incorporation of only biocompatible molecules and sterilisation.

Some of the cell culture solutions include:

Cell culture medium such as Dulbecco's Modified Eagle Medium (DMEM), Minimum Essential Media (MEM), Iscove's Modified Dulbecco's Medium (IMDM), Media 199, Ham's F10, Ham's F12, McCoy's 5A and Roswell Park Memorial Institute (RPMI) medium;

Growth supplements such as foetal calf serum (FCS), epidermal growth factor (EGF), basic fibroblast growth factor (bFBF), fibroblast growth factor (FBF), endothelial cell growth factor (ECGF), insulin-like growth factor 1 (IGF-1) and platelet-derived growth factor (PDGF);

Biological buffers such as PBS, HEPES and CHES;

Chelating and stabilizing solutions; and

Sterilized MilliQ water.

Cell-Culture Conditions

Cells and the 3D tissue culture models can be incubated, cultured and maintained using standard cell culture techniques. The 3D tissue culture models comprising the cells encapsulated in the hydrogel mold can be incubated under conditions to allow or maintain cell growth or spheroid formation. Incubation is typically carried out at about 37° C. with a CO2 level of 5% for at least 24 hours for most animal and human cell lines. It will be appreciated that incubation can be carried out at any suitable conditions, temperature and time duration that allows growth, maintenance or spheroid formation of the type of cell or cells in the hydrogel mold.

Utility Solutions

Utility solutions are defined as the solutions which do not come into contact with the cells but are used to clean and sterilise all printer surfaces exposed to the cells. These solutions may include:

Ethanol at the correct concentration;

Sterile MilliQ water;

Cell culture medium;

Detergent; and

Hydrogen peroxide solution (2 w/v % maximum concentration).

Preparation of Bio-Ink

Initially, bio-ink is prepared by mixing the right type and amount of macromolecules in the appropriate cell-culture solution. After achieving homogeneity, the blank bio-ink is sterilised via both UV irradiation and filtration (0.22 μm filter). The bio-ink is then kept at 4° C. until further usage.

Preparation of Cells

Harvest cells by washing with PBS. Aspirate PBS. Add trypsin and incubate at 37° C. to dissociate cells from flask surface. Add tissue culture media to collect dissociated cells into a tube. Centrifuge cells, aspirate supernatant and resuspend pellet in fresh media. Perform cell count by mixing equal volumes of cell suspension and trypan blue stain. Perform calculation to determine the cell concentration. Desired numbers of cells then can be added to bio-ink, cell-ink or added to cell culture solutions.

Preparation of Activators

The correct type and amount of molecules were dissolved in the appropriate cell-culture solution. The resulting solution was sterilised via UV irradiation and filtration prior to use.

Preparation of Cell-Ink

The correct type and amount of molecules were dissolved in the appropriate cell-culture solution. After achieving homogeneity, the resulting solution was sterilised via UV irradiation and filtration prior to use. The cell-ink was then kept at room temperature until further use.

Cell Harvesting

Cultured cells of interest at certain confluency are harvested by following the already established protocols. To make up the bio-ink or cell-ink containing cells, harvested cells are resuspended at the correct cell concentration to give 250 million cells/ml concentration in 200 µl of bio-ink or cell-ink. The resulting cell pellets are then redispersed in the correct volume of bio-ink or cell-ink. The bio-ink or cell-ink containing cells is then ready for use in the 3D bio-printer.

Printing of Hydrogel Mold

The hydrogel mold can be printed using a drop-on-drop process whereby a droplet of bio-ink and a droplet of activator were deposited on top of each other to produce a hydrogel. This process can be repeated and used to form 3D hydrogel structures by building up layers of hydrogel.

Cell Types 3D tissue culture models such as spheroids can be prepared from any suitable cell type including adherent cells such as mammalian liver cells, gastrointestinal cells, pancreatic cells, kidney cells, lung cells, tracheal cells, vascular cells, skeletal muscle cells, cardiac cells, skin cells, smooth muscle cells, connective tissue cells, corneal cells, genitourinary cells, breast cells, reproductive cells, endothelial cells, epithelial cells, fibroblast, neural cells, Schwann cells, adipose cells, bone cells, bone marrow cells, cartilage cells, pericytes, mesothelial cells, cells derived from endocrine tissue, stromal cells, stem cells, progenitor cells, lymph cells, blood cells, endoderm-derived cells, ectoderm-derived cells, mesoderm-derived cells, or combinations thereof.

Additional cell types may include other eukaryotic cells (e.g. chinese hamster ovary), bacteria (e.g. *Helicobacter pylori*), fungi (e.g. *Penicillium chrysogenum*) and yeast (e.g. *Saccharomyces cerevisiae*).

The cell line SK-N-BE(2) (neuroblastoma cells) has been used successfully in the process to produce 3D tissue culture models under a range of conditions. It will be appreciated that other cell lines would be expected to perform as required in 3D tissue models produced by the process developed. Other cell lines used include DAOY (human medulloblastoma cancer cells), H460 (human non-small lung cancer) and p53R127H (human pancreatic cancer cells). Other cell lines that may be suitable are listed on 088 and 089.

3D bio-printing technology was developed to produce high density 3D tissue culture models encapsulated in a hydrogel mold via drop-on-demand techniques. Specifically, a 3D printing technology was used to print biocompatible hydrogel molds using a bio-ink and activator that are constructed in a layer-by-layer manner to fabricate a variety of 3D structures. During the fabrication of the hydrogel molds, high cell density droplets can be included into the hydrogel mold.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Murphy, S. and Atala, A. (2014). 3D bioprinting of tissues and organs. Nature Biotechnol, 32(8), pp 773-785.

Horn, T. and Harrysson, O. (2012). Overview of current additive manufacturing technologies and selected applications. Sci. Prog, 95, pp 255-282.

The invention claimed is:

1. A bioprinter for fabricating three-dimensional (3D) cell constructs within a sterile environment, the bioprinter comprising:
   a housing encompassing:
   one or more holding reservoirs for holding a fluid sample;
   a printstage for holding a sample container and supporting a substrate on which a 3D cell construct is to be printed;
   a sample loading system in fluid communication with the one or more holding reservoirs, the sample loading system configured to automatically load a sample from a sample container into the one or more holding reservoirs;
   a pump in fluid communication with the sample loading system, the pump configured to draw the sample out of a sample container and pump the sample into the one or more holding reservoirs;
   a droplet dispensing system in fluid communication with the one or more holding reservoirs, the droplet dispensing system configured to print sample droplets from each of the one or more holding reservoirs onto the substrate supported by the printstage;
   wherein the droplet dispensing system is a separate element to the sample loading system;
   an air flow system integrated into the bioprinter, the air flow system configured to induce a laminar air flow within the housing;
   wherein the air flow system comprises a fan configured to draw air into the housing, an air inlet for the air to flow into, one or more filters and an air outlet; and
   wherein the air flow system integrated into the bioprinter provides the sterile environment for bioprinting of 3D cell constructs;
   wherein the sample loading system comprises a needle for insertion into a sample container, the pump configured to draw fluid through the needle when the needle is inserted into the sample container; and
   further comprising a first positioning unit coupled to the needle, the first positioning unit configured to insert the needle into a sample container and withdraw the needle from the sample container.

2. The bioprinter of claim 1, further comprising a second positioning unit having a track, the second positioning unit coupled to the needle and the droplet dispensing system and configured to move the needle and the droplet dispensing system along the track of the second positioning unit.

3. The bioprinter of claim 2, further comprising a third positioning unit having a track, the third positioning unit coupled to the print stage and configured to move the print stage along the track of the third positioning unit.

4. The bioprinter of claim 3 wherein the track of the second positioning unit extends substantially perpendicularly to the track of the third positioning unit.

5. The bioprinter of claim 1, wherein the one or more holding reservoirs comprises a plurality of holding reservoirs, and the sample loading system configured to load a sample from the sample container into any one of the plurality of holding reservoirs.

6. The bioprinter of claim 5, wherein the sample container is a tray having a plurality of sample wells, the sample wells configured to contain samples, and the sample loading system is configured to load a sample from any one of the sample wells into any one of the holding reservoirs.

7. The bioprinter of claim 6, further comprising a waste container configured to receive waste material from the sample loading system.

8. The bioprinter of claim 7, wherein the waste container is provided on the tray.

9. The bioprinter of claim 1, wherein the pump is configured to draw the sample out of one of the holding reservoirs and pump the sample out of the sample loading system.

10. The bioprinter of claim 1, further comprising a pressure regulator coupled in fluid communication to each holding reservoir to regulate the pressure in each holding reservoir.

11. The bioprinter of claim 10, further comprising a selector valve in fluid communication with the pump, the sample loading system, each holding reservoir, and the pressure regulator, the selector valve configured to selectively couple the pump in fluid communication to the sample loading system and each holding reservoir.

12. The bioprinter of claim 11, wherein the pressure regulator is removably coupled in fluid communication to a compressed air supply.

13. A method of fabricating a three-dimensional cell construct comprising depositing droplets of one or more samples using the bioprinter of claim 1.

14. A method of fabricating a three-dimensional cell construct, the method comprising:
providing a bioprinter of claim 1;
providing a substrate to the printstage;
providing a sample container to printstage, the sample container comprising a sample;
loading a sample into one of the holding reservoirs by the sample loading system; and
printing the sample onto the substrate from the holding reservoir using the droplet dispensing system to form the three-dimensional cell construct.

15. The bioprinter of claim 1, wherein the sample container is situated remotely from the one or more holding reservoirs.

16. The bioprinter of claim 1, wherein the pump is part of the sample loading system.

17. The bioprinter of claim 1, wherein the fan draws air into the front of the housing from underneath the printstage, around the sample loading system, and through one or more filters and out of the housing.

18. The bioprinter of claim 1, further comprising a sterile chamber consisting of the one or more filters, wherein at least one filter recycles airflow to the sterile chamber, the airflow from the filter recycling airflow to the sterile chamber providing unidirectional downward airflow to the sterile chamber.

* * * * *